US009365491B2

(12) United States Patent
Rishton et al.

(10) Patent No.: US 9,365,491 B2
(45) Date of Patent: Jun. 14, 2016

(54) INHIBITORS OF COGNITIVE DECLINE

(71) Applicant: COGNITION THERAPEUTICS, INC., Pittsburgh, PA (US)

(72) Inventors: Gilbert M. Rishton, Malibu, CA (US); Susan Catalano, Pittsburgh, PA (US)

(73) Assignee: COGNITION THERAPEUTICS, INC., Pittsburgh, PA (US)

( * ) Notice: Subject to any disclaimer, the term of this patent is extended or adjusted under 35 U.S.C. 154(b) by 0 days.

(21) Appl. No.: 14/293,755

(22) Filed: Jun. 2, 2014

(65) Prior Publication Data

US 2014/0371324 A1    Dec. 18, 2014

Related U.S. Application Data

(62) Division of application No. 13/263,162, filed as application No. PCT/US2010/030130 on Apr. 6, 2010, now Pat. No. 8,765,816.

(60) Provisional application No. 61/309,091, filed on Mar. 1, 2010, provisional application No. 61/308,667, filed on Feb. 26, 2010, provisional application No. 61/167,984, filed on Apr. 9, 2009.

(51) Int. Cl.
*A61K 31/55* (2006.01)
*A61K 31/45* (2006.01)
*A61K 31/40* (2006.01)
*C07C 211/27* (2006.01)
*C07C 217/62* (2006.01)

(52) U.S. Cl.
CPC ............. *C07C 211/27* (2013.01); *C07C 217/62* (2013.01)

(58) Field of Classification Search
None
See application file for complete search history.

(56) References Cited

U.S. PATENT DOCUMENTS

| 4,321,386 | A | 3/1982 | Lawson |
|---|---|---|---|
| 4,697,024 | A | 9/1987 | Donaldson |
| 6,011,068 | A | 1/2000 | Nemeth |
| 6,057,371 | A | 5/2000 | Glennon |
| 6,518,315 | B1 | 2/2003 | Roufogalis et al. |
| 6,991,814 | B2 | 1/2006 | Ray et al. |
| 7,723,377 | B2 | 5/2010 | Rishton et al. |
| 2004/0033277 | A1 | 2/2004 | Ray et al. |
| 2007/0021413 | A1 | 1/2007 | Herold et al. |
| 2008/0101757 | A1 | 5/2008 | Lin |
| 2008/0103107 | A1 | 5/2008 | Ward |
| 2008/0153917 | A1 | 6/2008 | Ellis |
| 2008/0193573 | A1 | 8/2008 | Gow et al. |
| 2008/0193574 | A1 | 8/2008 | Rishton et al. |
| 2009/0017038 | A1 | 1/2009 | Colabufo |
| 2009/0022667 | A1 | 1/2009 | Peters |
| 2009/0035295 | A1 | 2/2009 | Hillen |
| 2010/0028333 | A1 | 2/2010 | Getty |
| 2010/0029654 | A1 | 2/2010 | Pasinetti |
| 2011/0082154 | A1 | 4/2011 | Oksenberg |
| 2011/0111068 | A1 | 5/2011 | Rishton et al. |

FOREIGN PATENT DOCUMENTS

| CA | 2073841 A1 | 1/1993 |
|---|---|---|
| DE | 4000610 | 7/1991 |
| DE | 10320560 A1 | 1/2004 |
| EP | 0881220 A1 | 12/1998 |
| JP | 2003113117 | 4/2003 |
| WO | WO 01/30335 A2 | 5/2001 |
| WO | 2006020879 A1 | 2/2006 |
| WO | WO 2006/138349 A1 | 12/2006 |
| WO | 2007077543 | 7/2007 |
| WO | WO 2008/042755 A2 | 4/2008 |
| WO | WO 2009/054468 A1 | 4/2009 |
| WO | 2009059214 A1 | 5/2009 |
| WO | WO 2010/062260 A1 | 6/2010 |
| WO | WO 2010/118055 A1 | 10/2010 |
| WO | WO 2011/014880 A1 | 2/2011 |
| WO | 2011106785 | 9/2011 |
| WO | 2013029057 A2 | 2/2013 |

OTHER PUBLICATIONS

Aboul-Enein et al., Synthesis of certain 1, 7, 7-trimethylbicyclo (2.2.1) heptane derivatives with anticonfulsant, hypoglycemic and anti-inflammatory potential, (2006), CASREACT 147:10056 (Accession No. 2006:599283).

Arai et al., Chemically conditioned extracts of ginger oil; leadlike "alkaloidal" compounds derived from natural extracts via reductive animation. General Biochemistry, Biotechnology and Pharmaceutical—Poster, Wednesday, Jan. 25, 2006 (Laguna (DoubleTree Hotel)).

Barghorn et al., Globular amyloid β-peptide$_{1-42}$ oligomer—a homogenous and stable neurophathological protein in Alzheimer's disease, *J. Neurochem.* (Nov. 2005), 95(3):834-847.

Begum et al., Curcumin Structure-Function, Bioavailability, and Efficacy in Models of Neuroinflammation and Alzheimer's Disease, *The Journal of Pharmacology and Experimental Therapeutics* (Feb. 4, 2008), 326(1): 196-208.

Brody et al., Amyloid-β Dynamics Correlate with Neurological Status in the Injured Human Brain, *Science* (Aug. 29, 2008), 321(5893): 1221-1224.

Bu. Apolipoprotein E and its receptors in Alzheimer's disease: pathways, pathogenesis and therapy, *Nat Rev Neurosci.* (May 2009). 10(5):333-344.

(Continued)

*Primary Examiner* — Jeffrey S Lundgren
*Assistant Examiner* — Michael Schmitt
(74) *Attorney, Agent, or Firm* — Leason Ellis LLP

(57) ABSTRACT

Compounds that are central nervous system drug candidates for the treatment of cognitive decline and, more particularly, Alzheimer's disease are provided. Methods of treating, inhibiting, and/or abatement of cognitive decline and/or Alzheimer's disease with a compound or pharmaceutically acceptable salt of the invention are also provided. Also provided are methods of preparing the compounds/compositions of the invention.

20 Claims, 4 Drawing Sheets

(56) References Cited

OTHER PUBLICATIONS

Calabrese et al., Rapid, concurrent alternations in pre- and postsynaptic structure induced by naturally-secreted Amyloid-β protein, *Mol. Cell. Neurosci.* (Feb. 2, 2007), p. 1-11.
Catalano et al., The role of Amyloid-β derived diffusible ligands (ADDLs) in Alzheimer's disease, *Curr Top Med Chem.* (2006), 6(6):597-608.
Chang, et al., AMPA receptor downscaling at the onset of Alzheimer's disease pathology in double knockin mice, *PNAS* (Feb. 28, 2006), 103(9):3410-3415.
Chin et al., Fyn kinase induces synaptic and cognitive impairments in a transgenic mouse model of Alzheimer's disease, *J. Neurosci.* (Oct. 19, 2005), 25(42);9694-9703.
Cirrito et al., Endocytosis is required for synaptic activity-dependent release of Amyloid-β in vivo, *Neuron.* (Apr. 10, 2008), 58(1):42-51.
Citron et al., Evidence that the 42- and 40-amino acid forms of amyloid beta protein are generated from the beta-amyloid precursor protein by different protease activities, *Proc. Nat. Acad. Sci. USA* (Nov. 1996), 93:13170-13175.
Citron, Strategies for Disease Modification in Alzheimer's Disease, *Nat Rev Neurosci.* (Sep. 2004), 5(9):677-685.
Cleary et al., Natural oligomers of the Amyloid-β protein specifically disrupt cognitive function, *Nat Neurosci.* (Jan. 2005), 8(1):79-84.
Craig et al., How to build a central synapse: clues torn cell culture, *Trends Neurosci.* (Jan. 2006), 29(1):8-20.
Crawford et al. "Metalation of limonene. Novel method for the synthesis of bisabolane sesquiterpenes." *J. of the Am. Chm. Soc.* (Jun. 14, 1972) 94(12):4298-4306.
Dahlgren et al., Oligomeric and Fibrillar Species of Amyloid-β Peptides Differentially Affect Neuronal Viability, *J Biol Chem.* (Aug. 30, 2002), 277(35)32046-32053.
De Felice et al., Targeting the neurotoxic species in Alsheimer's disease: inhibitors of Aβ oligomerization, *FASEB J.* (Sep. 2004), 18(12):1366-1372.
Dedov et al., Gingerols: a novel class of vanilloid receptor (VR1) agonists, *Br. J. of Pharm.* (Nov. 2002), 137(6):793-798.
Denniff, Syntheses of the (±)-[n]-Gmgerois (Pungent Principles of Ginger) and Related Compounds through Regioselective Aldol Condensations: Relative Pungency Assays, *J Chem. Soc. Perkin* 1 (Nov. 2002), pp. 82-87.
Diverse Approaches to Alzheimer's Therapies Continue to Show Progress at ICAD, International Conference on Alzheimer's Disease 2008 (Jul. 26-31, 2008), Chicago, Illinois.
Dodart et al., Immunization reverses memory deficits without reducing brain Aβ burden in Alzheimer's disease model. *Nat Neurosci* (May 2002), 5(5):452-457.
Doody et al., Effect of dimebon on cognition, activities of daily living, behavior; and global function in patients with mild-to-moderate Alzheimer's disease; a randomised, double-blind, placebo-controlled study, *Lancet* (Jul. 19, 2008), 372(9634):207-215.
Fenili et al., Properties of *scyllo*-inositol as a therapeutic treatment of AD-like pathology, *J Mol Med.* (Jun. 2007), 85(6):603-611.
Flood et al., FAD mutant PS-1 gene-targeted mice: Increased Aβ42 and Aβ deposition without APP overproduction, *Neurobiol Aging* (May-Jun. 2002), 23(3):335-348.
Fukumoto et al., Beta-Secretase Activity Increases with Aging in Human, Monkey, and Mouse Brain, *Am. J. of Path.* (Feb. 2004), 164(2):719-725.
Georganopoulou et al., Nanoparticle-based detection in cerebral spinal fluid of a soluble pathogenic biomarker for Alzheimer's disease, *PNAS* (Feb. 15, 2005), 102(7):2273-2276.
Golde, Alzheimer disease therapy: can the Amyloid cascade be halted?, *J Clin Invest.* (Jan. 2003), 111(1):11-18.
Gortz et al., Neuronal network properties of human teratocarcinoma cell line-derived neurons. *Brain Res* (Aug. 20, 2004), 1018(1):18-25.
Grazanna et al. "Ginger—An herbal medicinal product with broad anti-inflammatory actions." *J. of Medicinal Food*, (Jul. 1, 2005) 8(2):125-132.

Griffith et al., Elevated brain scyllo-inositol concentrations in patients with Alzheimer's disease, *NMR Biomed* (Dec. 2007), 20(8):709-716.
Grzanna et al., Ginger Extract Inhibits Beta-Amyloid Peptide-Induced Cytokine and Chemokine Expresion in Cultured THP-1 Monocytes, *J. of Altern. & Complem, Med*, (2004), 10:1009-1013.
Hampel et al., Core candidate neurochemical and imaging biomarkers of Alzheimer's disease, *Alzheimers Dement* (Jan. 2008), 4(1):38-48.
Hansson et al., Reduced Levels of Amyloid-β-Binding Proteins in Cerebrospinal Fluid from Alzheimer's Disease Patients, *J Alzheimers Dis* (2009), 16(2):389-397.
Hisahai et al. Heptatoprotective Consituents from Zedoariae Rhizoma: Absolute Stereostructures of Three New Carabrane-type Sesquiterpenes, Curcumenolactones A, B, and C. *Bioorganic & Med. Chem.* 9 (2001): 909-916.
Hisashi et al. Medicinal Foods. XXVIII 1) Inhibitors of Nitric Oxide Production and New Sesquiterpenes, Zedoarofuran, 4-Epicurcumenol, Neocurcumenol, Gajutsulactones A and By, y and Zedoarolides A and B, from Zedoariae Rhizoma. Chem. *Pharm. Bull.*(2001) 49(12) 13-15 1558-1566.
Ho et al., Heterogeneity in red wine polyphenolic contents differentially influences Alzheimer's disease-type neuropathology and cognitive deterioration, *J Alzheimers Dis.* (2009), 16(1):59-72.
Hong et al., Candidate anti-Aβ fluorine compounds selected from analogs of Amyloid imaging agents, *Neurobiol Aging.* (Oct. 2010), 31(10): 1690-1699.
Hong et al., Combining the rapid MTT formazan exocytosis assay and the MC65 protection assay led to the discovery of carbazole analogs as small molecule inhibitors of Aβ oligomer- induced cytotoxicity. *Brain Res* (Jan. 26, 2007), 1130(1):223-234.
Hong et al., Inhibition of Alzheimer's Amyloid toxicity with a trycyclic pyrone molecule in vitro and in vivo. *J Neurochem.* (Feb. 2009), 108(4):1097-1108.
Hsieh et al., AMPAR removal underlies Aβ-induced synaptic depression and Dendritic spine loss. *Neuron.* (Dec. 7, 2006), 52(5); 831-843.
International Search Report and Written Opinion for PCT/US2007/79850 dated Jun. 3, 2008.
International Search Report and Written Opinion for PCT/US2010/30130 dated Jun. 10, 2010.
International Search Report and Written Opinion for PCT/US2010/44136 dated Sep. 24, 2010.
International Search report for US2011/026530 dated Jun. 30, 2012.
International Search report for US2012/023483 dated May 31, 2012.
Jacobsen et al., GSI-953 Is a Protein APP-Selective Gamma-Secretase Inhibitor for the *Treatment of Alzheimer's Disease*, Oral 03-06: Therapeutics and Therapeutic Strategies: Novel Targets (2008), p. 139.
Jin et al., Novel tricyclic pyrone compounds prevent intracellular APP C99-induced cell death, *J Mol Neurosci* (Aug.-Oct. 2002), 19(1-2):57-61.
Johansson et al., Physiochemical characterization of the Alzheimer's disease-related peptides Aβ1-42Arctic and Aβ1-42wt, *FEBS J.* (Jun. 2006). 273(12):2618-2630.
Kaech et al., Culturing hippocampal neurons, *Nat Protoc* (2006), 1(5):2406-2415.
Kamal et al. "Total synthesis of (R)-and (S)-turmerone and (7S,9R)-bisacumol by an efficient chemoenymatic approach." *Tetrahedron:Asymmetry*. (Jun. 19, 2009), 20(11):1267-1271.
Kamenetz et al., APP processing and synaptic function. *Neuron.* (Mar. 27, 2003), 37(6):925-937.
Kimura, Chemical Structural Requirement in Gingeroi Derivatives for Potentiation of Prostaglandin F2 alpha-induced Contraction in Isolated Mesenteric Veins of Mice, *J. Pharmacobio-Dyn.* (1989), 12:220-227.
Klyubin et al., Amyloid β Protein Dimer-Containing Human CSF Disrupts Synaptic Plasticity; Prevention by Systemic Passive Immunization, *J Neurosci.* (Apr. 16, 2008), 28(16):4231-4237.
Klyubin et al., Amyloid β protein immunotherapy neutralizes Aβ oligomers that disrupt synaptic plasticity in vivo, *Nat Med* (May 2005), 11(5):556-561.

(56) References Cited

OTHER PUBLICATIONS

Koffie et al., Oligomeric amyloid β associates with postsynaptic densities and correlates with excitatory synapse loss near senile plaques, *Proc. Natl Acad Sci USA* (Mar. 10, 2009), 106(10):4012-4017.
Kornhuber et al., Cerebrospinal fluid and serum concentrations of the N-methyl-$_D$-aspartate (NMDA) receptor antagonist memantine in man. *Neurosci Lett* (Aug. 4, 1995), 195(2):137-139.
Kottlinek et al., Reversible memory loss in a mouse transgenic model of Alzheimer's disease, *J Neurosci* (Aug. 1, 2002), 22(15):6331-6335.
Lacor et al., Aβ oligomer-induced aberrations in synapse composition, shape, and density provide a molecular basis for loss and connectivity in Alzheimer's disease, *J Neurosci.* (Jan. 24, 2007), 27(4):796-807.
Lacor et al., Synaptic targeting by Alzheimer s-related Amyloid β oligomers, *J Neurosci.* (Nov. 10, 2004), 24(45):10191-10200.
Lambert et al., Diffusible, nonfibrillar ligands derived from Aβ$_{1-42}$ are potent central nervous system neurotoxins, *Proc Natl Acad Sci USA* (May 26, 1998), 95(11):6448-6453.
Lambert et al., Monoclonal antibodies that target pathological assemblies of Aβ *J Neurochem* (Jan. 2007), 100(1):23-35.
Lannfelt et al., Safety, efficacy, and biomarker findings of PBT2 in targeting Aβ as a modifying therapy for Alzheimer's disease; a phase IIa, double-blind, randomised, placebo-controlled trial, *Lancet Neurol* (Sep. 2008), 7(9):779-786.
Lauren et al., Cellular prion protein mediates impairment of synaptic plasticity by Amyloid-β oligomers *Nature.* (Feb. 26, 2009), 457(7233):1128-1132.
Lecanu et al., Identification of naturally occurring spirostenols preventing β-amyloid-induced neurotoxicity. *Steroids* (Jan. 2004), 69(1): 1-16.
Lesne et al., A specific amyloid-β protein assembly in the brain impairs memory. *Nature* (Mar. 16, 2006), 440(7082):352-357.
Levine, Alzheimer's β-peptide oligomer formation at physiologic concentrations. *Anal Biochem* (Dec. 1, 2004), 335(1):81-90.
Li et al., Soluble oligomers of Amyloid β protein facilitate hippocampal long-term depression by disrupting neuronal glutamate uptake. *Neuron.* (Jun. 25, 2009), 62(6):788-801.
Liu et al., Cytotoxic Amyloid Peptides Inhibit Cellular 3-(4,5-Dimethyithiazol-2yl)-2,5- Diphenyltetrazolium Bromide (MTT) Reduction by Enhancing MTT Formazan Exocytosis, *J Neurochem.* (Dec. 1997), 69(6):2285-2293.
Liu et al., Detecting bioactive Amyloid β peptide species in Alzheimer's disease, *J Neurochem.* (Nov. 2004), 91:648-656.
Liu et al., Treating Alzheimer's Disease by Inactivating Bioactive Amyloid β Peptide, *Curr Alzheimer Res* (Apr. 2006), 3(2):129-135.
Lleo, et al., Clinical, pathological, and biochemical spectrum of Alzheimer disease associated with PS-1 mutations, *Am J Geriatr Psychiatry* (Mar.-Apr. 2004), 12(2):146-156.
Look et al., Discovery of ADDL—Targeting Small Molecule Drugs for Alzheimer's disease, *Curr Alzheimer Res.* (Dec. 2007), 4(5): 562-567.
Maezawa et al., A novel tricyclic pyrone compound ameliorates cell death associated with intracellular Amyloid-β oligomeric complexes, *J Neurochem.* (Jul. 2006), 98(1):57-67.
Majno, Apoptosis, oncosis, and necrosis: an overview of cell death. *Am J Pathol.* (Jan. 1995), 146(1):3-15.
Mann et al., Amyloid angiopathy and variability in Amyloid β deposition is determined by mutation position in presenilin-1-linked Alzheimer's disease. *Am J Pathol.* (Jun. 2001), 158(6):2165-2175.
Masuda et al., Antioxidant properties of gingerol related compounds from ginger, *Biofactors* (2004), 21(14):293-296.
Masuda et al., Antioxidant properties of gingerol related compounds from ginger, *BioFactors* (2004), 21:293-296.
Matsubara et al., Soluble Aβ homeostasis in AD and DS: impairment of anti-amyloidogenic protection by lipoproteins, *Neurobiol Aging* (Aug. 2004), 25(7):833-841.
Matsuda et al. Medicinal foodstuffs. XXVIII. Inhibitors of nitric oxide production and new sesquiterpenes, zedoarofuran, 4-epicurcumenol, neocumenol, gajutsulactones A and B, and zedoarolides A and B, from Sedoariae Rizoma, Chemical and Pharmaceutical Bulletin, *Pharmaceutical Society of Japan*, (Dec. 1, 2001), 49(12):1558-1566.
Mayer et al., Discovery of Begacestat, a Notch-1-Sparing γ-Secretase Inhibitor for the Treatment of Alzheimer's Disease, *J Med Chem* (Oct. 3, 2008), 51:7348-7351.
Miklossy et al., Two novel presenilin-1 mutations (Y256S and Q222H) are associated with early-onset Alzheimer's disease. *Neurobiol Aging* (Sep. 2003),. 24(5):655-662.
Morris, D.O. Hebb: The Organization of Behavior, Wiley, New York (1949), *Brain Research Bulletin* (May 19, 1999), 50(5-6):437-438.
Morris, Episodic-like memory in animals: psychological criteria, neural mechanisms and the value of episodic-like tasks to investigate animal models of neurodegenerative disease, *Philos Trans R Soc Lond B Biol Sci.* (Sep. 29, 2001), 356(1413):1453-1465.
Mucke et al., High-level neuronal expression of Aβ$_{1-42}$ in wild-type human Amyloid protein precursor transgenic mice: synaptotoxicity without plaque formation, *J Neuroscience.* (Jun. 1, 2000), 20(11):4050-4058.
Mustafa et al., Drug Development Report (9): Pharmacology of Ginger, *Zingiber Officinale. J. Drug. Dev.* (1993), 6(1):25-39.
Negron et al., Study of the asymmetric induction of the 1,3-dipolar cycloaddition of chiral azomethine ylides with unactivated double bonds, CASREACT 117:26230 (Accession No. 1992:426230) (1992).
Nielsen et al., Binding and Uptake of Aβ1-42 by Primary Human Astrocytes In Vitro, *GLIA* (2009), 57:978-988.
Nikolaev et al., APP binds DR6 to trigger axon pruning and neuron death via distrinct caspases, *Nature* (Feb. 19, 2009), 457(7232):981-989.
Nomura et al., Mechanism of impairment of long-term potentiation by Amyloid β is independent of NMDA receptors or voltage-dependent calcium channels in hippocampal CA1 pyramidal neurons, *Neurosci Lett.* (Dec. 31, 2005), 391(1-2):1-6.
Ono et al. Effects of grape seed-derived polyphenols on Amyloid β-protein self-assembly and cytotoxicity, *J Biol Chem.* (Nov. 12, 2008), 283(47):32176-32187.
Poling et al., Oligomers of the Amyloid-β protein disrupt working memory: confirmation with two behavioral procedures, *Behav Brain Res.* (Nov. 21, 2008), 193(2):230-234.
Price et al., Neuron number in the entorhinal cortex and CA1 in preclinical Alzheimer disease. *Arch Neurol.* (Sep. 2001), 58(9):1395-1402.
Priller et al., Mutant presenilin 1 alters synaptic transmission in cultured hippocampal neurons, *J Biol Chem.* (Jan. 12, 2007), 282(2):1119-1127.
Puzzo et al., Amyloid-β Peptide Inhibits Activation of the Nitric Oxide/cGMP/cAMP-Responsive Element-Binding Protein Pathway during Hippocampal Synaptic Plasticity, *J Neurosci* (Jul. 20, 2005), 25(29):6887-6897.
Puzzo et al., Picomolar Amyloid-β positively modulates synaptic plasticity and memory in hippocampus, *J Neurosci.* (Dec. 31, 2008), 28(53):14537-14545.
Rana et al., Syntheses of tricyclic pyrones and pyridinones and protection of Aβ-peptide induced MC65 neuronal cell death, *BioorgMed Chem Lett* (Feb. 1, 2009), 19(3):670-674.
Rishton et al., Computational approaches to the prediction of blood-brain barrier permeability: a comparative analysis of central nervous system drugs versus secretase inhibitors for Alzheimer's disease, *Curr Opin Drug Discov Devel* (May 2006), 9(3):303-313.
Rishton et al., Computational approaches to the prediction of blood-brain barrier permeability: A comparative analysis of central nervous system drugs versus secretase inhibitors for Alzheimer's disease, *Curr. Opin. in Drug Discov. & Dev.* (2006), 9(3):303-313.
Rishton, Nonleadlikeness and leadlikeness in biochemical screening. *Drug Discov Today* (Jan. 15, 2003). 8(2):86-96.
Rishton, Reactive compounds and in vitro false positives in HTS, *DDT* (Sep. 9, 1997), 2(9)382-384.
Ronicke et al., Aβ mediated diminution of MTT reduction—an artefact of single cell culture?, *PLoS One* (Sep. 18, 2008), 3(9):e3236.

(56) References Cited

OTHER PUBLICATIONS

Rowan et al., Mechanisms of the inhibitory effects of Amyloid β-protein on synaptic plasticity, *Exp Gerontol.* (Nov.-Dec. 2004), 39(11-12):1661-1667.
Sampson et al., Metal protein attenuating compounds for the treatment of Alzheimer's disease (review). The Cochrane Collaboration, published in The Cochrane Library (2009), Issue 1.
Scheff et al., Hippocampal synaptic loss in early Alzheimer's disease and mild cognitive impairment, *Neurobiol Aging* (Oct. 2006), 27(10):1372-1384.
Scheff et al., Synaptic alternations in CA1 mild Alzheimer disease and mild cognitive impairment. *Neurology* (May 1, 2007), 68:1501-1507.
Sejnowski et al., The Book of Hebb: Minireivew, *Neuron* (Dec. 1999), 24:773-776.
Shankar et al., Amyloid-β protein dimers isolated directly from Alzheimer's brains impair synaptic plasticity and memory, *Nat Med*, (Aug. 2008). 14(8):837-842.
Shankar et al., Natural oligomers of the Alzheimer Amyloid-β protein induce reversible synapse loss by modulating an NMDA-type glutamate receptor-dependent signaling pathway, *J Neurosci.* (Mar. 14, 2007), 27(11):2866-2875.
Shin et al., Zingerone as an Antioxidant against Peroxynitrite, *J. of Agric. & Food Chem.* (2005), 53:7617-7622.
Shrestha et al., Amyloid β peptide adversely affects spine number and motility in hippocampal neurons. *Mol Cell Neurosci* (Nov. 2006), 33(3):274-282.
Snyder et al., Regulation of NMDA receptor trafficking by Amyloid-β, *Nat Neurosci.* (Aug. 2005), 8(8):1051-1058.
Surh et al., Enzymic Reduction of [6]-Gingerol, a Major Pungent Principle of Ginger, in the Cell-Free Preparation of Rat Liver, *Life Sci.* (1994), 54(19):321-326.
Terry, Cell death or synaptic, loss in Alzheimer disease, *J Nuropathol Exp Neurol.* (Dec. 2000), 59(12):1118-1119.
Ting et al., Amyloid precursor protein overexpression depresses excitatory transmission through both presynaptic and postsynaptic mechanisms, *Proc Natl Acad Sci USA* (Jan. 2, 2007), 104(1):353-358.
Tomiyama et al., A New Amyloid Variant Favoring oligomerization in Alzheimer's-type dementia, *Ann Neurol* (Mar. 2008), 63(3):377-387.
Tong et al., β-amyloid peptide at sublethal concentrations downregulates brain-derived neurotrophic factor functions in cultured cortical neurons. *J Neurosci.* (Jul. 28, 2004), 24(30):6799-6809.
Townsend et al., Orally available compound prevents deficits in memory caused by the Alzheimer Amyloid-β oligomers, *Ann. Neurol* (Dec. 2006). 60(6):668-676.
Verdile et al., The role of beta amyloid in Alzheimer's disease: still a cause of everything or the only one who got caught?, *Pharmacol Res* (Oct. 2004), 50(4):397-409.
Walsh et al., Certain inhibitors of synthetic Amyloid β-peptide (Aβ) fibrillogenesis block oligomerization of natural Aβ and thereby rescue long-term potentiation, *J Neurosci.* (Mar. 9, 2005), 25(10):2455-2462.
Walsh et al., Naturally secreted oligomers of Amyloid β protein potently inhibit hippocampal long-term potentiation in vivo. *Nature* (Apr. 4, 2002), 416(6880):535-539.
Wang et al., Block of Long-Term Potentiation by Naturally Secreted and Synthetic Amyloid β-Peptide in Hippocampal Slices is Mediated Via Activation of the Kinases c-Jun N-Terminal Kinase, Cyclin-Dependent Kinase 5, and p38 Mitogen-Activated Protein Kinase as well as Metabotropic Glutamate Receptor Type 5, *J Neurosci.* (Mar. 31, 2004), 24(13):3370-3378.
Wang et al., Grape-derived polyphenolics prevent Aβ oligomerization and attenuate cognitive deterioration in a mouse model of Alzheimer's disease, *J Neurosci.* (Jun. 18, 2008), 28(25):6388-6392.
Wang et al., Moderate consumption of Cabernet Sauvignon attenuates Aβ neuropathology in a mouse model of Alzheimer's disease,*FASEB J.* {Nov. 2006), 20(13):2313-2320.
Wang et al., Soluble oligomers of β Amyloid (1-42) inhibit long-term potentiation but not long-term depression in rat dentate gyms. *Brain Res*, (Jan. 11, 2002), 924(2): 133-140.
West et al., Hippocampal neurons in pre-clinical Alzheimer's disease, *Neurobiol Aging* (Oct. 2004), 25(9):1205-1212.
Whitlock et al., Learning induces long-term potentiation in the hippocampus, *Science* (Aug. 25, 2006), 313(5790):1093-1097.
Wolozin, Cholesterol and the Biology of Alzheimer's Disease, *Neuron* (Jan. 8, 2004), 41:7-10.
Yao et al., The *Ginkgo biloba* extract EGb 761 rescues the PC 12 neuronal cells from β-amyloid-induced cell death by inhibiting the formation of β-amyloid-derived diffusible neurotoxic ligands, *Brain Res.* (Jan. 19, 2001). 889(1-2):181-190.
Yu et al., Per-6-Substituted β-Cyclodextrin Libraries Inhibit Formation of β-Amyloid-Peptide (Aβ)-Derived, Soluble Oligomers, *J Mol Neurosci* (Aug.-Oct. 2002), 19(1-2):51-55.
Zhang et al. Chiral Benzyl Centers through Asymmetric Catalysis. A Three-Step Synthesis of (R)-(−)-Alpha-Curcumene via Asymmetric Hydrovinylations, *Organic Letter*, (Aug. 3, 2004) 6(18):3160-3161.
Zhang et al., A Simple Statistical Parameter for Use in Evaluation and Validation of High Throughput Screening Assays, *J Biomol Screen* (1999), 4(2):67-73.
Zhao et al., Identification of antihypertensive drugs which inhibit Amyloid-β protein oligomerization, *J Alzheimers Dis.* (2009), 16(1):49-57.
Zlokovic, New therapeutic targets in the neurovascular pathway in Alzheimer's disease, *Neurotherapeutics* (Jul. 2008), 5(3):409-414.
Extended European Search Report by the European Patent Office, dated Apr. 15, 2015, for European Patent Application No. 12824979.4 (12 pages).
International Search Report and Written Opinion for International Application No. PCT/US2012/052572 mailed Feb. 25, 2013 (13 pages).
International Search Report and Written Opinion for International Application No. PCT/US2012/052578 mailed Jan. 18, 2013 (12 pages).
Ishikawa; et al., "The role of sigma-1 receptors in the pathophysiology of neuropsychiatric diseases", Journal of Receptor, Ligand and Channel Research (2009), retrieved from: http://www.researchgate.net/profile/Masatomo_Ishikawa/publication/49606716_The_role_of_sigma-1_receptors_in_the_pathophysiology_of_Neuropsychiatric_diseases/.
Maier; et al., "Synthesis and SAR Studies of 3-Substituted 1'-Benzylspiro[[2]benzoxepine1,4'-piperidines]", European Journal of Organic Chemistry (Feb. 2003), 2003(4):714-720.
Maurice; et al., "The pharmacology of sigma-1 receptors", Pharmacology and Therapeutics (Nov. 2009), 124 (2):195-206.
Office Action w/English translation, from Chinese Patent Office dated Jun. 17, 2015, for Chinese Patent Application No. 201280052588.4, 17 pgs.
Office Action w/English translation, from Chinese Patent Office dated Mar. 31, 2015, for Chinese Patent Application No. 201280052595.4, 14 pgs.
Supplementary European Search Report, from European Patent Office dated Sep. 21, 2015, for European Patent Application No. 12825341.6 (filed Aug. 27, 2012), 19 pgs.
Leal, P. et al. Functional Properties of Spice Extracts Obtained via Supercritical Fluid Extraction, Journal of Agricultural and Food Chemistry (2003), 51(9), 2520-2525 (Derwent Abstract).
International Search Report and Written Opinion for International Application No. for PCT/US2010/044136 dated Sep. 24, 2010, (12 pages).
Walsh et al., Certain inhibitors of synthetic Amyloid .beta.-peptide (A.beta.) fibrillogenesis block oligomerization of natural A.beta. and thereby rescue long-term potentiation, J Neurosci. (Mar. 9, 2005), 25(10):2455-6392.
Adams et al., The Leaf Essential Oils and Taxonomy of Juniperus oxycedrus L. subsp. oxycedrus, subsp. badia (H. Gay) Debeaux, and subsp. macrocarpa (Sibth. & Sm.) Ball, J.Essent. Oil Res., Mar./Apr. 1999, 11:167-172.
Balaji et al., Toxicity Prediction of Compounds from Turmeric, Food and Chemical Toxicology, 2010, vol. 48, 2951-2959.

(56) References Cited

OTHER PUBLICATIONS

Banerjee et al., Chemical Modification of Turmeric Oil to More Value Added Products, Indian Perfumer, 1981, vol. 25, pp. 25-30.
Chang et al., Supercritical carbon dioxide extraction of turmeric oil from Curcuma Ionga Linn and purification of turmerones, Separation and Purification Technology, (2006), 47:119-125.
Fujiwara et al., Acetylcholinesterase Inhibitory Activity of Volatile Oil from Peltophorum dasyrachis Kurz ex Bakar (Yellow Batai) and Bisabolane-Type Sesquiterpenoids, Journal of Agricultural and Food Chemistry, 58(5):2824-2829 (Jan. 2010).
Gopalan et al., Supercritical Carbon Dioxide Extraction of Tumeric (Curcuma Ionga), J. Agric. Food Chem., (2000), 48:2189-2192.
Krafft et al., ADDLs and the signaling web that leads to Alzheimer\s disease, Neuropharmacology, (2010), 59:230-242.
Levine, Biotin-avidin interaction-based screening assay for Alzheimer\s [2]-peptide oligomer inhibitors, Analytical Biochemistry, (2006), 356:265-272.
Li et al., Total asymmetric synthesis of (7S, 9R)-(+)-bisacumol, Tetrahedrom: Asymmetry, (2003), 14:75-78.
Mori et al., Synthesis of a Mixture of (+-)-Dehydrojuvabione and its Stereoisomer, Tetrahedron Letters, 48:4853-4856 (1967).
Uehara et al., New Bisabolane Sesquiterpenoids from the Rhizomes of Curuma Xanthorrhiza (Zinziberaceae), Chemical and Pharmaceutical Bulletin, 37 (1):237-240 (1989).
Weiyan et al., Research Advances on Chemistry and Pharmacology of Zingiber officinale, Chinese Journal of Ethnomedicine and Ethnopharmacology, 2008(9).
Database CA Chemical Abstracts Service, Columbus, OH, Park et al., retrieved from STN Database Accession No. 1989:8424, Archives of Pharmacal Research, 10(4), 239-44 (1987).
Database CA Chemical Abstracts Service, Columbus, OH, Duchene et al., retrieved from STN Database Accession No. 1986:479177, Synthetic Communications, 15(10):873-882 (1985).
Database CA Chemical Abstracts Service, Columbus, OH, Alexander et al., retrieved from STN Database Accession No. 1971:541008; Indian Journal of Chemistry, 9(8), 776-9 (1971).

a. Vehicle (N=10)

b. Abeta (N=10)

c. Compound Example 2 (1 pmol) + Abeta (N=12)

d. Compound Example 2 (2 pmol) + Abeta (N=9)

INHIBITORS OF COGNITIVE DECLINE

This application is a Division of U.S. application Ser. No. 13/263,162, filed 20 Dec. 2011, now U.S. Pat. No. 8,765,816, issued Jul. 1, 2014, which is a National Stage Application of PCT/US2010/030130, filed 6 Apr. 2010, in turn claiming benefit of U.S. Provisional Ser. No. 61/309,091, filed 1 Mar. 2010, U.S. Provisional Ser. No. 61/308,667, filed 26 Feb. 2010 and U.S. Provisional Ser. No. 61/167,984, filed 9 Apr. 2009. All of the foregoing applications are incorporated herein by reference.

SUMMARY

The present invention provides, inter alia, compounds of Formula I, II, or III:

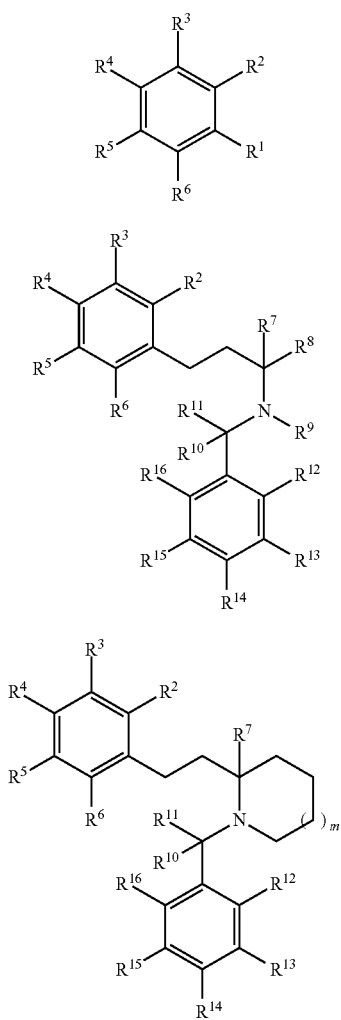

or pharmaceutically acceptable salts, wherein constituent members are provided below.

The present invention further provides pharmaceutical compositions comprising a compound of Formula I, II, or III, or pharmaceutically acceptable salt thereof, and at least one pharmaceutically acceptable carrier.

The present invention further provides methods of inhibiting, treating, and/or abating cognitive decline and/or Alzheimer's disease with a compound of Formula I, II, or III, or pharmaceutically acceptable salt of the same.

The present invention further provides methods of inhibiting, treating, or abatement of cognitive decline with a compound of Formula I, II, or III, or pharmaceutically acceptable salt of the same.

The present invention further provides methods of inhibiting, treating, or abatement of one or more of amyloid production, amyloid assembly, amyloid aggregation, amyloid binding (to cells in the brain such as neuron cells), the activity/effect of Abeta oligomers on neurons, and amyloid deposition (on cells in the brain such as neuron cells) with a compound of Formula I, II, or III, or pharmaceutically acceptable salt of the same.

The present invention further provides compounds of Formula I, II, or III, or pharmaceutically acceptable salts thereof, for use in therapy.

The present invention further provides use of the compounds of Formula I, II, or III, or pharmaceutically acceptable salts thereof, for the manufacture/preparation of a medicament for use in therapy.

In some embodiments, methods for preparation of compounds useful for inhibiting, treating, or abatement of cognitive decline are provided. In a method called "chemical conditioning", certain compounds of the present invention are derived from naturally occurring compounds, such as those found in medicinal plants, like ginger. The chemical conditioning process described herein is applicable to a large variety of biological extracts and may be used to create compound arrays for screening for potential new drug candidates. Further, in general, compounds derived by the chemical conditioning process are chemically stable and structurally diverse, and good candidates for use in drug screenings for pharmaceutical activity. In some embodiments, compounds derived from ginger oil are provided. According to some embodiments of the invention, compounds derived from ginger oil by the chemical conditioning process described herein are provided. In another embodiment, the invention provides a method of preparing an array of chemical compounds from ginger oil.

In some embodiments, the compounds of present invention inhibit, treat, or abate (partially inhibit) binding of the amyloid (including Abeta oligomers) to neurons (such as neurons in the brain) and are useful for the inhibition, treatment, and abatement of cognitive decline and/or Alzheimer's disease. In some embodiments, the compounds of present invention inhibit, treat, or abate one or more of amyloid aggregation, amyloid binding, and amyloid deposition. In some embodiments, the compounds of present invention inhibit, treat, or abate amyloid aggregation. In some embodiments, the compounds of present invention inhibit, treat, or abate amyloid binding. In some embodiments, the compounds of present invention inhibit, treat, or abate amyloid deposition. In some embodiments, the compounds of present invention inhibit, treat, or abate the activity/effect of Abeta oligomers on neurons. In some embodiments, the compounds show activity in a beta-secretase assay and are potentially useful for the inhibition, treatment, and abatement of cognitive decline and Alzheimer's disease. In some embodiments the derivative of ginger oil is a compound in purified and isolated form (for example, with a purity of greater than 80%, 85%, 90%, 95%, 98%, or 99% by weight). The compounds and methods described herein may be used to treat one or more symptoms of cognitive decline and/or Alzheimer's disease such as memory loss, confusion, impaired judgment, personality changes, disorientation, and loss of language skills. Further, the compounds and methods described herein may be useful in inhibiting, treating, and/or abating cognitive decline and/or Alzheimer's disease by restoring long term potentiation, and/or inhibiting, treating, or abatement of one or both of neurodegeneration and general amyloidosis, more specifically, by inhibiting, treating, or abatement of one or more of amyloid production, amyloid assembly, amyloid aggregation, amyloid binding, and amyloid deposition.

DETAILED DESCRIPTION

Figure 1:
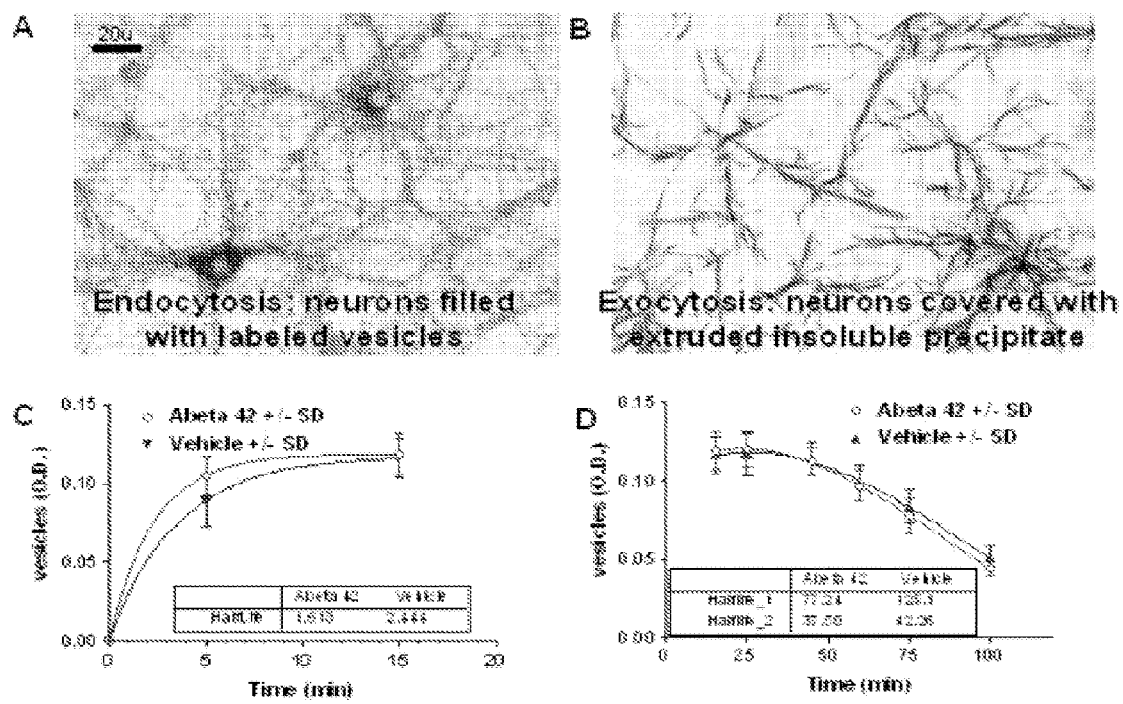
FIG. 1 shows results of an MTT assay in the presence and absence of a processed product of amyloid precursor protein.

Cognitive decline, such as memory loss, confusion, impaired judgment, personality changes, disorientation, and loss of language skills occurs in much of the population as they age, in varying degree. The most common, severe and irreversible form of cognitive decline is Alzheimer's disease, which, at present, is always fatal.

The symptoms of cognitive decline and Alzheimer's disease are thought to stem from the formation of amyloid plaques and neurofibrillary tangles, which are thought to contribute to the degradation of the neurons (nerve cells) in the brain and the subsequent onset of symptoms. Amyloid is a general term for protein fragments that the body produces normally. Beta-amyloid is a fragment of a protein that is snipped from another protein called amyloid precursor protein (APP). In a healthy brain, beta-amyloid protein fragments are broken down and eliminated. In individuals with Alzheimer's disease and other forms of cognitive decline, the fragments accumulate to form hard, insoluble plaques. Neurofibrillary tangles are insoluble twisted fibers that are found inside of the brain's cells. The protein contained in neurofibrillary tangles, i.e., the tau protein, forms a microtubule, which helps transport nutrients and other important substances from one part of the nerve cell to another. In Alzheimer's disease the tau protein is abnormal and the microtubule structures collapse.

Beta-secretase is the enzyme in the human brain responsible for the production of Beta-amyloid, the pathogenic substance responsible for the formation of brain plaques and tangles in the Alzheimer's diseased brain. Beta-amyloid and its oligomers (beta-amyloid oligomers or Abeta oligomers) are also believed to be responsible for early cognitive decline in the pre-Alzheimer's diseased brain. Inhibition of beta-secretase would be expected to lessen beta-amyloid burden in the brain and thus slow cognitive decline, block the formation of amyloid oligomers, the production of plaques and tangles, halt neurodegeneration, and to potentially treat mild cognitive impairment and more serious forms of cognitive impairment such as Alzheimer's disease.

The gingerols are a series of natural small molecules isolated from ginger, *Zingiber officinale*, and are classified according to their alkyl chain length e.g., [6]-gingerol, [8]-gingerol. Gingerols are known to be relatively unstable under both chemical and biological conditions, forming inactive substances. For example, the beta-hydroxycarbonyl function of the gingerols is vulnerable to oxidation or dehydration to form inactive products, and the gingerols are particularly prone to rapid dehydration under acidic conditions, such that even the pure substance is difficult to store for long periods. Accordingly, simple oral dosing of the gingerols for medicinal action might not be possible due to the acidic environment of the stomach and upper intestinal tract. Further, chemical and biological instability is also likely to be a serious problem for intravenous doses. Accordingly, there is strong need to discover inhibitors of cognitive decline, and in particular, compounds that are useful in the treatment and abatement of cognitive decline and Alzheimer's disease, by methods such as inhibiting amyloid (including Abeta oligomers) production, amyloid (including Abeta oligomers) aggregation, and/or amyloid (including Abeta oligomers) deposition (i.e., plaqing), inhibiting neuorodegeneration, and/or restoring long term potentiation, and/or inhibiting the activity/effect of Abeta oligomers on neurons. There is also a need for inhibitors of cognitive decline that are chemically and biologically stable.

Plants have attracted relatively little attention as potentially valuable resources for drug discovery in the area of cognitive decline and Alzheimer's disease. The use of plant extracts to produce unnatural derivatives of compounds of medicinal interest is not generally used. Accordingly, there is also a need for a method of producing compounds of medicinal interest from plant extracts and extracts from other biological sources. In particular, there is also a need to produce and identify compounds derived from plant extracts that are useful in the treatment and abatement of cognitive decline and Alzheimer's disease.

The compounds, compositions, and methods described herein are directed toward these needs and other ends.

Embodiments of the present invention provides, inter alia, compounds of Formula I:

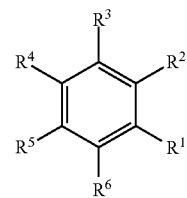

or pharmaceutically acceptable salts thereof wherein:

$R^1$ is selected from (A1) and (A2):

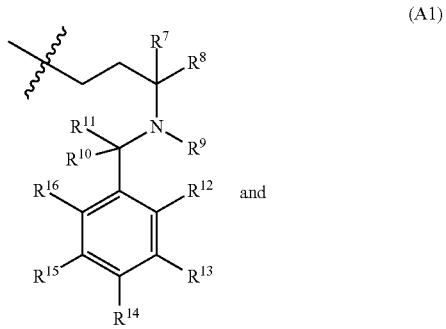

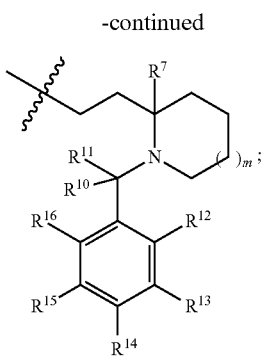

(A2)

$R^2$, $R^3$, $R^4$, $R^5$, and $R^6$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), $C(O)OR^a$, $C(O)R^b$, $C(O)NR^cR^d$, $OC(O)R^b$, $OC(O)NR^cR^d$, $NR^cR^d$, $NR^cC(O)R^b$, $NR^cC(O)OR^a$, $NR^cS(O)_2R^b$, $NR^cS(O)_2NR^cR^d$, $S(O)R^b$, $S(O)_2R^b$, and $S(O)_2NR^cR^d$;

$R^7$ is H, $C_{1-6}$ alkyl, $C_{1-6}$ haloalkyl, or $C_{3-7}$cycloalkyl;
$R^8$ is $C_{1-6}$ alkyl, $C_{1-6}$ haloalkyl, or $C_{3-7}$ cycloalkyl;
$R^9$ is H, $C_{1-6}$ alkyl, $C_{1-6}$ haloalkyl, or $C_{3-7}$cycloalkyl;
$R^{10}$ is H, $C_{1-6}$ alkyl, $C_{1-6}$ haloalkyl, or $C_{3-7}$ cycloalkyl;
$R^{11}$ is H, $C_{1-6}$ alkyl, $C_{1-6}$ haloalkyl, or $C_{3-7}$ cycloalkyl;
$R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), $C(O)OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{a1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{b1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

$R^{c1}$ and $R^{d2}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl; and m is 0, 1, or 2.

In some embodiments, when $R^1$ is a moiety of (A1), then two of $R^2$, $R^3$, $R^4$, $R^5$, and $R^6$ are independently selected from OH, $C_{1-6}$ alkoxy, and $C_{1-6}$ haloalkoxy.

In some embodiments, when $R^1$ is a moiety of (A1), then at least one of $R^{12}$, $R^{13}$, $R^{14}$, $R^{15}$, and $R^{16}$ is other than H.

In some embodiments, two of $R^2$, $R^3$, $R^4$, $R^5$, and $R^6$ are independently selected from OH, $C_{1-6}$ alkoxy, and $C_{1-6}$ haloalkoxy. In some further embodiments, each of the rest of $R^2$, $R^3$, $R^4$, $R^5$, and $R^6$ is H.

In some embodiments, $R^2$, $R^3$, $R^4$, $R^5$, and $R^6$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$cycloalkyl), $N(C_{1-4}$ alkyl$)_2$, $NHC(O)(C_{1-4}$ alkyl), SH, $S(C_{1-6}$ alkyl), C(O)OH, $C(O)O(C_{1-4}$ alkyl), $C(O)(C_{1-4}$ alkyl), and $C(O)NH(C_{1-4}$ alkyl).

In some embodiments, one of $R^2$, $R^3$, $R^4$, $R^5$, and $R^6$ is OH; and one of $R^2$, $R^3$, $R^4$, $R^5$, and $R^6$ is OH, $C_{1-6}$ alkoxy, or $C_{1-6}$ haloalkoxy. In some further embodiments, each of the rest of $R^2$, $R^3$, $R^4$, $R^5$, and $R^6$ is H.

In some embodiments, one of $R^2$, $R^3$, $R^4$, $R^5$, and $R^6$ is OH; and one of $R^2$, $R^3$, $R^4$, $R^5$, and $R^6$ is $C_{1-3}$ alkoxy or $C_{1-3}$ haloalkoxy (In some further embodiments, each of the rest of $R^2$, $R^3$, $R^4$, $R^5$, and $R^6$ is H.). In some further embodiments, one of $R^2$, $R^3$, $R^4$, $R^5$, and $R^6$ is OH; and one of $R^2$, $R^3$, $R^4$, $R^5$, and $R^6$ is methoxy or trihalomethoxy (In some further embodiments, each of the rest of $R^2$, $R^3$, $R^4$, $R^5$, and $R^6$ is H.). In still further embodiments, one of $R^2$, $R^3$, $R^4$, $R^5$, and $R^6$ is OH; and one of $R^2$, $R^3$, $R^4$, $R^5$, and $R^6$ is methoxy (In some further embodiments, each of the rest of $R^2$, $R^3$, $R^4$, $R^5$, and $R^6$ is H.).

In some embodiments, $R^4$ is OH; and $R^5$ is methoxy. In some further embodiments, $R^4$ is OH; $R^5$ is methoxy; and $R^2$, $R^3$, and $R^6$ are each H.

In some embodiments, $R^7$ is H or $C_{1-6}$ alkyl. In some further embodiments, $R^7$ is H or $C_{1-3}$ alkyl.

In some embodiments, $R^7$ is $C_{1-3}$ alkyl. In some further embodiments, $R^7$ is methyl or ethyl. In still further embodiments, $R^7$ is methyl.

In some embodiments, $R^7$ is H.

In some embodiments, $R^8$ is $C_{1-6}$ alkyl. In some further embodiments, $R^8$ is $C_{1-3}$ alkyl.

In still further embodiments, $R^8$ is methyl.

In some embodiments, $R^9$ is H or $C_{1-6}$ alkyl. In some further embodiments, $R^9$ is H or $C_{1-3}$ alkyl.

In some embodiments, $R^9$ is H.

In some embodiments, $R^9$ is $C_{1-3}$ alkyl.

In some embodiments, $R^{10}$ is H or $C_{1-6}$ alkyl. In some further embodiments, $R^{10}$ is H or $C_{1-3}$ alkyl. In still further embodiments, $R^{10}$ is H. In other embodiments, $R^{10}$ is $C_{1-3}$ alkyl.

In some embodiments, $R^{11}$ is H or $C_{1-6}$ alkyl. In some further embodiments, $R^{11}$ is H or $C_{1-3}$ alkyl. In still further embodiments, $R^{11}$ is H. In other embodiments, $R^{11}$ is $C_{1-3}$ alkyl.

In some embodiments, at least one of $R^{12}$, $R^{13}$, $R^{14}$, $R^{15}$, and $R^{16}$ is other than H.

In some embodiments, $R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), C(O)OH, $C(O)O(C_{1-4}$ alkyl), $C(O)(C_{1-4}$ alkyl), and $C(O)NH(C_{1-4}$ alkyl).

In some embodiments, $R^{12}$, $R^{13}$, $R^{14}$, $R^{15}$, and $R^{16}$ are each, independently, selected from H, halo, CN, $NO_2$, $C_{1-6}$ alkyl, $C_{1-6}$ haloalkyl, $C_{3-7}$ cycloalkyl, $C(O)O(C_{1-4}$ alkyl), $C(O)(C_{1-4}$ alkyl), and $C(O)NH(C_{1-4}$ alkyl).

In some embodiments, at least one of $R^{12}$, $R^{13}$, $R^{14}$, $R^{15}$, and $R^{16}$ is selected from halo, CN, $NO_2$, $C_{1-6}$ haloalkyl, $C(O)O(C_{1-4}$ alkyl), $C(O)(C_{1-4}$ alkyl), and $C(O)NH(C_{1-4}$ alkyl).

In some embodiments, at least one of $R^{12}$, $R^{13}$, $R^{14}$, $R^{15}$, and $R^{16}$ is selected from halo and $C_{1-6}$ haloalkyl. In some further embodiments, at least one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H. In yet further embodiments, one or two of $R^{12}$, $R^{13}$, $R^{14}$, $R^{15}$, and $R^{16}$ are selected from halo and $C_{1-6}$ haloalkyl, and each of the rest is of $R^{12}$, $R^{13}$, $R^{14}$, $R^{15}$, and $R^{16}$ is H. In still further embodiments, one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H.

In some embodiments, $R^{14}$ is halo or $C_{1-6}$ haloalkyl (In some further embodiments, each of $R^{12}$, $R^{13}$, $R^{15}$, and $R^{16}$ is H.). In some further embodiments, $R^{14}$ is halo or $C_{1-3}$ haloalkyl (In some further embodiments, each of $R^{12}$, $R^{13}$, $R^{15}$, and $R^{16}$ is H.). In still further embodiments, $R^{14}$ is halo or $C_1$ haloalkyl (In some further embodiments, each of $R^{12}$, $R^{13}$, $R^{15}$, and $R^{16}$ is H.).

In some embodiments, $R^{14}$ is halo (In some further embodiments, each of $R^{12}$, $R^{13}$, $R^{15}$, and $R^{16}$ is H.). In some embodiments, $R^{14}$ is Cl or F. In some embodiments, $R^{14}$ is Cl. In some embodiments, $R^{14}$ is F.

In some embodiments, $R^{14}$ is $C_{1-6}$ haloalkyl (In some further embodiments, each of $R^{12}$, $R^{13}$, $R^{15}$ and $R^{16}$ is H.). In some embodiments, $R^{14}$ is $C_{1-3}$ haloalkyl. In still further embodiments, $R^{14}$ is $C_1$ haloalkyl. In yet further embodiments, $R^{14}$ is $CF_3$.

In some embodiments, $R^{15}$ is halo or $C_{1-6}$ haloalkyl (In some further embodiments, each of $R^{12}$, $R^{13}$, $R^{14}$, and $R^{16}$ is H.). In some further embodiments, $R^{15}$ is halo or $C_{1-3}$ haloalkyl (In some further embodiments, each of $R^{12}$, $R^{13}$, $R^{14}$, and $R^{16}$ is H.). In still further embodiments, $R^{15}$ is halo or $C_1$ haloalkyl (In some further embodiments, each of $R^{12}$, $R^{13}$, $R^{14}$, and $R^{16}$ is H.).

In some embodiments, $R^{15}$ is halo. In some embodiments, $R^{15}$ is Cl or F. In some embodiments, $R^{15}$ is Cl. In some embodiments, $R^{15}$ is F.

In some embodiments, $R^{15}$ is $C_{1-6}$ haloalkyl. In some further embodiments, $R^{15}$ is $C_{1-3}$ haloalkyl. In still further embodiments, $R^{15}$ is $C_1$ haloalkyl. In yet further embodiments, $R^{15}$ is $CF_3$.

In some embodiments, $R^{14}$ and $R^{15}$ are each independently halo or $C_{1-3}$ haloalkyl (In some further embodiments, each of $R^{12}$, $R^{13}$, and $R^{16}$ is H.). In some further embodiments, $R^{14}$ and $R^{15}$ are each independently halo or $C_1$ haloalkyl.

In some embodiments, $R^{14}$ and $R^{15}$ are each independently halo.

In some embodiments, the compound of Formula I is a compound of Formula II:

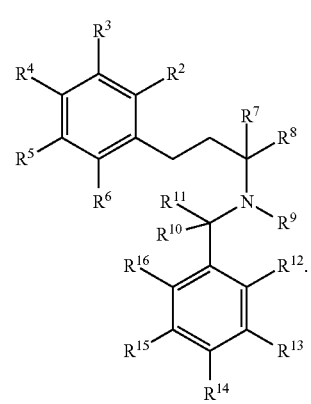

II

In some embodiments, the compound of Formula II or pharmaceutically acceptable salt thereof is a compound of Formula IIa or IIb:

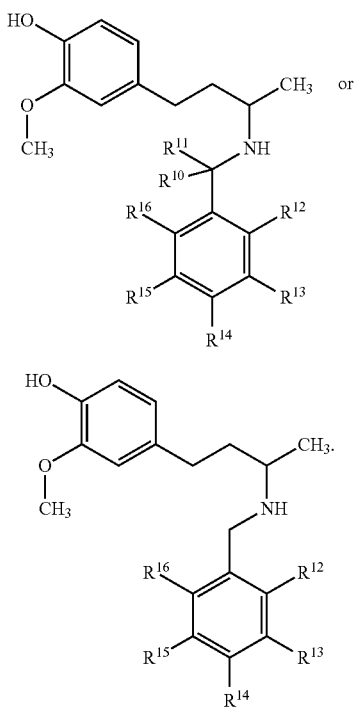

or pharmaceutically acceptable salt thereof.

In some embodiments, the compound of Formula II is a compound of Formula IIa. In some further embodiments, $R^{10}$ and $R^{11}$ are each, independently, selected from H and $C_{1-3}$ alkyl. In yet further embodiments, $R^{10}$ and $R^{11}$ are each, independently, selected from H and methyl. In still further embodiments, $R^{10}$ and $R^{11}$ are each H.

In some embodiments of the compound of Formula IIa or pharmaceutically acceptable salt thereof, one of $R^{10}$ and $R^{11}$ is selected from H and $C_{1-3}$ alkyl and the other is H. In some further embodiments, one of $R^{10}$ and $R^{11}$ is $C_{1-3}$ alkyl. In yet further embodiments, one of $R^{10}$ and $R^{11}$ is methyl.

In some embodiments of the compound of Formula IIa or pharmaceutically acceptable salt thereof, both of $R^{10}$ and $R^{11}$ are selected from $C_{1-3}$ alkyl. In some further embodiments, both $R^{10}$ and $R^{11}$ are methyl.

In some embodiments of the compound of Formula IIa or pharmaceutically acceptable salt thereof, $R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), C(O)OH, $C(O)O(C_{1-4}$ alkyl), $C(O)(C_{1-4}$ alkyl), and $C(O)NH(C_{1-4}$ alkyl).

In some embodiments of the compound of Formula IIa or pharmaceutically acceptable salt thereof, $R^{12}$, $R^{13}$, $R^{14}$, $R^{15}$, and $R^{16}$ are each, independently, selected from H, halo, CN, $NO_2$, $C_{1-6}$ alkyl, $C_{1-6}$ haloalkyl, $C_{3-7}$ cycloalkyl, $C(O)O(C_{1-4}$ alkyl), $C(O)(C_{1-4}$ alkyl), and $C(O)NH(C_{1-4}$ alkyl).

In some embodiments of the compound of Formula IIa or pharmaceutically acceptable salt thereof, $R^{12}$, $R^{13}$, $R^{14}$, $R^{15}$, and $R^{16}$ are each, independently, selected from H, halo, CN, $NO_2$, $C_{1-6}$ alkyl, $C_{1-6}$ haloalkyl, and $C_{3-7}$ cycloalkyl. In some further embodiments, $R^{12}$, $R^{13}$, $R^{14}$, $R^{15}$, and $R^{16}$ are each, independently, selected from H, halo, CN, $C_{1-6}$ alkyl and $C_{1-6}$ haloalkyl. In yet further embodiments, $R^{12}$, $R^{13}$, $R^{14}$, $R^{15}$, and $R^{16}$ are each, independently, selected from H, halo, $C_{1-6}$ alkyl, and $C_{1-6}$ haloalkyl.

In some embodiments of the compound of Formula IIa or pharmaceutically acceptable salt thereof, at least one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H. In some further embodiments, one or two of $R^{12}$, $R^{13}$, $R^{14}$, $R^{15}$, and $R^{16}$ are selected from halo and $C_{1-6}$ haloalkyl, and each of the rest is of $R^{12}$, $R^{13}$, $R^{14}$, $R^{15}$, and $R^{16}$ is H. In yet further embodiments, one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H.

In some embodiments of the compound of Formula IIa or pharmaceutically acceptable salt thereof, at least one of $R^{12}$, $R^{13}$, $R^{14}$, $R^{15}$, and $R^{16}$ is selected from halo, CN, $NO_2$, $C_{1-6}$ haloalkyl, $C(O)O(C_{1-4}$ alkyl), $C(O)(C_{1-4}$ alkyl), and $C(O)NH(C_{1-4}$ alkyl).

In some embodiments of the compound of Formula IIa, at least one of $R^{12}$, $R^{13}$, $R^{14}$, $R^{15}$, and $R^{16}$ is selected from halo and $C_{1-6}$ haloalkyl.

In some embodiments of the compound of Formula IIa or pharmaceutically acceptable salt thereof, at least one of $R^{12}$, $R^{13}$, $R^{14}$, $R^{15}$, and is selected from halo and $C_{1-3}$ haloalkyl. In some further embodiments, at least one of $R^{12}$, $R^{13}$, $R^{14}$, $R^{15}$ and $R^{16}$ is selected from halo and $C_1$ haloalkyl.

In some embodiments of the compound of Formula IIa or pharmaceutically acceptable salt thereof, $R^{14}$ is halo or $C_{1-6}$ haloalkyl. In some further embodiments, $R^{14}$ is halo or $C_{1-3}$ haloalkyl. In still further embodiments, $R^{14}$ is halo or $C_1$ haloalkyl.

In some embodiments of the compound of Formula IIa or pharmaceutically acceptable salt thereof, $R^{14}$ is halo (In some further embodiments, each of $R^{12}$, $R^{13}$, $R^{15}$, and $R^{16}$ is H.). In some embodiments, $R^{14}$ is Cl or F. In some embodiments, $R^{14}$ is Cl. In some embodiments, $R^{14}$ is F.

In some embodiments of the compound of Formula IIa, $R^{14}$ is $C_{1-6}$ haloalkyl (In some further embodiments, each of $R^{12}$, $R^{13}$, $R^{15}$, and $R^{16}$ is H.). In some further embodiments, $R^{14}$ is $C_{1-3}$ haloalkyl. In still further embodiments, $R^{14}$ is $C_1$ haloalkyl. In yet further embodiments, $R^{14}$ is $CF_3$.

In some embodiments of the compound of Formula IIa or pharmaceutically acceptable salt thereof, $R^{14}$ is halo or $C_{1-6}$ haloalkyl and each of $R^{12}$, $R^{13}$, $R^{15}$, and $R^{16}$ is H.

In some embodiments of the compound of Formula IIa or pharmaceutically acceptable salt thereof, $R^{15}$ is halo or $C_{1-6}$ haloalkyl (In some further embodiments, each of $R^{12}$, $R^{13}$, $R^{14}$, and $R^{16}$ is H.). In some embodiments, $R^{15}$ is halo or $C_{1-3}$ haloalkyl. In still further embodiments, $R^{15}$ is halo or $C_1$ haloalkyl.

In some embodiments of the compound of Formula IIa or pharmaceutically acceptable salt thereof, $R^{15}$ is halo. In some embodiments, $R^{15}$ is Cl or F. In some embodiments, $R^{15}$ is Cl. In some embodiments, $R^{15}$ is F.

In some embodiments of the compound of Formula IIa or pharmaceutically acceptable salt thereof, $R^{15}$ is $C_{1-6}$ haloalkyl. In some further embodiments, $R^{15}$ is $C_{1-3}$ haloalkyl. In still further embodiments, $R^{15}$ is $C_1$ haloalkyl. In yet further embodiments, $R^{15}$ is $CF_3$.

In some embodiments of the compound of Formula IIa or pharmaceutically acceptable salt thereof, $R^{14}$ and $R^{15}$ are each independently halo or $C_{1-3}$ haloalkyl (In some further embodiments, each of $R^{12}$, $R^{13}$, and $R^{16}$ is H.). In some further embodiments, $R^{14}$ and $R^{15}$ are each independently halo or $C_1$ haloalkyl. In yet further embodiments, $R^{14}$ and $R^{15}$ are each independently halo.

In some embodiments, the compound of Formula II or pharmaceutically acceptable salt thereof is a compound of Formula IIb or pharmaceutically acceptable salt thereof.

In some embodiments of the compound of Formula IIb or pharmaceutically acceptable salt thereof, $R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$cycloalkyl, $NH_2$, $NH(C_{1-4}$ alkyl), $NH(C_{3-7}$cycloalkyl), $N(C_{1-4}$ alkyl)$_2$, $NHC(O)(C_{1-4}$ alkyl), SH, $S(C_{1-4}$ alkyl), C(O)OH, $C(O)O(C_{1-4}$ alkyl), $C(O)(C_{1-4}$ alkyl), and $C(O)NH(C_{1-4}$ alkyl).

In some embodiments of the compound of Formula IIb or pharmaceutically acceptable salt thereof, $R^{12}$, $R^{13}$, $R^{14}$, $R^{15}$, and $R^{16}$ are each, independently, selected from H, halo, CN, $NO_2$, $C_{1-6}$ alkyl, $C_{1-6}$ haloalkyl, $C_{3-7}$ cycloalkyl, $C(O)O(C_{1-4}$ alkyl), $C(O)(C_{1-4}$ alkyl), and $C(O)NH(C_{1-4}$ alkyl).

In some embodiments of the compound of Formula IIb or pharmaceutically acceptable salt thereof, $R^{12}$, $R^{13}$, $R^{14}$, $R^{15}$, and $R^{16}$ are each, independently, selected from H, halo, CN, $NO_2$, $C_{1-6}$ alkyl, $C_{1-6}$ haloalkyl, and $C_{3-7}$ cycloalkyl. In some further embodiments, $R^{12}$, $R^{13}$, $R^{14}$, $R^{15}$, and $R^{16}$ are each, independently, selected from H, halo, CN, $C_{1-6}$ alkyl, and $C_{1-6}$ haloalkyl. In yet further embodiments, $R^{12}$, $R^{13}$, $R^{14}$, $R^{15}$, and $R^{16}$ are each, independently, selected from H, halo, $C_{1-6}$ alkyl, and $C_{1-6}$ haloalkyl.

In some embodiments of the compound of Formula IIb or pharmaceutically acceptable salt thereof, at least one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H. In some further embodiments, one or two of $R^{12}$, $R^{13}$, $R^{14}$, $R^{15}$, and $R^{16}$ are selected from halo and $C_{1-6}$ haloalkyl, and each of the rest is of $R^{12}$, $R^{13}$, $R^{14}$, $R^{15}$, and $R^{16}$ is H. In yet further embodiments, one of $R^{12}$, $R^{13}$, $R^{14}$, $R^{15}$, and $R^{16}$ is selected from halo and $C_{1-6}$ haloalkyl, and each of the rest is of $R^{12}$, $R^{13}$, $R^{14}$, $R^{15}$, and $R^{16}$ is H.

In some embodiments of the compound of Formula IIb or pharmaceutically acceptable salt thereof, at least one of $R^{12}$, $R^{13}$, $R^{14}$, $R^{15}$, and $R^{16}$ is selected from halo, CN, $NO_2$, $C_{1-6}$ haloalkyl, $C(O)O(C_{1-4}$ alkyl), $C(O)(C_{1-4}$ alkyl), and $C(O)NH(C_{1-4}$ alkyl).

In some embodiments of the compound of Formula IIb, at least one of $R^{12}$, $R^{13}$, $R^{14}$, $R^{15}$, and $R^{16}$ is selected from halo and $C_{1-6}$ haloalkyl.

In some embodiments of the compound of Formula IIb or pharmaceutically acceptable salt thereof, at least one of $R^{12}$, $R^{13}$, $R^{14}$, $R^{15}$, and $R^{16}$ is selected from halo and $C_{1-3}$ haloalkyl. In some further embodiments, at least one of $R^{12}$, $R^{13}$, $R^{14}$, $R^{15}$, and $R^{16}$ is selected from halo and $C_1$ haloalkyl.

In some embodiments of the compound of Formula IIb or pharmaceutically acceptable salt thereof, $R^{14}$ is halo or $C_{1-6}$ haloalkyl. In some further embodiments, $R^{14}$ is halo or $C_{1-3}$ haloalkyl. In still further embodiments, $R^{14}$ is halo or $C_1$ haloalkyl.

In some embodiments of the compound of Formula IIb or pharmaceutically acceptable salt thereof, $R^{14}$ is halo (In some further embodiments, each of $R^{12}$, $R^{13}$, $R^{15}$, and $R^{16}$ is H.). In some embodiments, $R^{14}$ is Cl or F. In some embodiments, $R^{14}$ is Cl. In some embodiments, $R^{14}$ is F.

In some embodiments of the compound of Formula IIb, $R^{14}$ is $C_{1-6}$ haloalkyl (In some further embodiments, each of $R^{12}$, $R^{13}$, $R^{15}$, and $R^{16}$ is H.). In some further embodiments, $R^{14}$ is $C_{1-3}$ haloalkyl. In still further embodiments, $R^{14}$ is $C_1$ haloalkyl. In yet further embodiments, $R^{14}$ is $CF_3$.

In some embodiments of the compound of Formula IIb or pharmaceutically acceptable salt thereof, $R^{14}$ is halo or $C_{1-6}$ haloalkyl and each of $R^{12}$, $R^{13}$ $R^{15}$, and $R^{16}$ is H.

In some embodiments of the compound of Formula IIb or pharmaceutically acceptable salt thereof, $R^{15}$ is halo or $C_{1-6}$ haloalkyl (In some further embodiments, each of $R^{12}$, $R^{13}$, $R^{14}$, and $R^{16}$ is H.). In some further embodiments, $R^{15}$ is halo or $C_{1-3}$ haloalkyl. In still further embodiments, $R^{15}$ is halo or $C_1$ haloalkyl.

In some embodiments of the compound of Formula IIb or pharmaceutically acceptable salt thereof, $R^{15}$ is halo. In some embodiments, $R^{15}$ is Cl or F. In some embodiments, $R^{15}$ is Cl. In some embodiments, $R^{15}$ is F.

In some embodiments of the compound of Formula IIb or pharmaceutically acceptable salt thereof, $R^{15}$ is $C_{1-6}$ haloalkyl. In some further embodiments, $R^{15}$ is $C_{1-3}$ haloalkyl. In still further embodiments, $R^{15}$ is $C_1$ haloalkyl. In yet further embodiments, $R^{15}$ is $CF_3$.

In some embodiments of the compound of Formula IIb or pharmaceutically acceptable salt thereof, $R^{14}$ and $R^{15}$ are each independently halo or $C_{1-3}$ haloalkyl (In some further embodiments, each of $R^{12}$, $R^{13}$, and $R^{16}$ is H.). In some further embodiments, $R^{14}$ and $R^{15}$ are each independently halo or $C_1$ haloalkyl. In yet further embodiments, $R^{14}$ and $R^{15}$ are each independently halo.

In some embodiments, the compound of Formula I is a compound of Formula III:

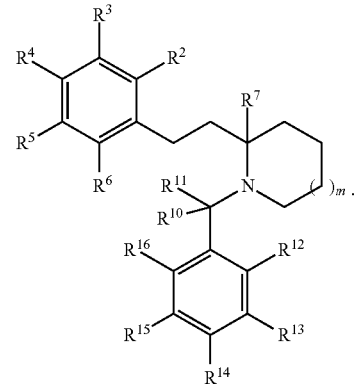

III

In some embodiments of compounds of Formula III or pharmaceutically acceptable salt thereof, m is 1.

In some embodiments of compounds of Formula III or pharmaceutically acceptable salt thereof, m is 0.

In some embodiments of compounds of Formula III or pharmaceutically acceptable salt thereof, at least one of $R^2$, $R^3$, $R^4$, $R^5$, and $R^6$ is selected from OH, $C_{1-6}$ alkoxy, and $C_{1-6}$ haloalkoxy.

In some embodiments of compounds of Formula III or pharmaceutically acceptable salt thereof, at least two of $R^2$, $R^3$, $R^4$, $R^5$, and $R^6$ are independently selected from OH, $C_{1-6}$ alkoxy, and $C_{1-6}$ haloalkoxy.

In some embodiments of compounds of Formula III or pharmaceutically acceptable salt thereof, at least one of $R^{12}$, $R^{13}$, $R^{14}$, $R^{15}$, and $R^{16}$ is other than H.

In some embodiments of the compound of Formula III or pharmaceutically acceptable salt thereof, $R^{14}$ and $R^{15}$ are each independently halo or $C_{1-3}$ haloalkyl. In some further embodiments, $R^{14}$ and $R^{15}$ are each independently halo or $C_1$ haloalkyl.

At various places in the present specification, substituents of compounds of the invention are disclosed in groups or in ranges. It is specifically intended that embodiments the invention include each and every individual subcombination of the members of such groups and ranges. For example, the term "$C_{1-6}$ alkyl" is specifically intended to individually disclose methyl ($C_1$ alkyl), ethyl ($C_2$ alkyl), $C_3$ alkyl, $C_4$ alkyl, $C_5$ alkyl, and $C_e$ alkyl.

For compounds of the invention in which a variable appears more than once, each variable can be a different moiety selected from the Markush group defining the variable. For example, where a structure is described having two R groups that are simultaneously present on the same compound, then the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents. Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic (e.g., having 2, 3 or 4 fused rings) ring systems as well as spiro ring systems. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cycloalkyl group can be optionally substituted by oxo or sulfido. Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl). Preferably, "cycloalkyl" refers to cyclized alkyl groups that contain up to 20 ring-forming carbon atoms. Examples of cycloalkyl preferably include cyclopropyl, cyclobutyl, cyclopentyl, cyclohexyl, cycloheptyl, adamantyl, and the like.

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Hetercycloalkyl groups can be mono or polycyclic (e.g., both fused and spiro systems). Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ring-forming carbon atoms and heteroatoms of a heterocycloalkyl group can be optionally substituted by oxo or sulfido. For example, a ring-forming S atom can be substituted by 1 or 2 oxo [i.e., form a S(O) or $S(O)_2$]. For another example, a ring-forming C atom can be substituted by oxo (i.e., form carbonyl). Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is $OCF_3$. As used herein, "trihalomethoxy" refers to a methoxy group having three halogen substituents. Examples of trihalomethoxy groups include, but are not limited to, —$OCF_3$, —$OCClF_2$, —$OCCl_3$, and the like.

As used herein, "arylalkyl" refers to a $C_{1-6}$ alkyl substituted by aryl and "cycloalkylalkyl" refers to $C_{1-6}$ alkyl substituted by cycloalkyl.

As used herein, "heteroarylalkyl" refers to a $C_{1-6}$ alkyl group substituted by a heteroaryl group, and "heterocycloalkylalkyl" refers to a $C_{1-6}$ alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used here, C(O) refers to C(=O).
As used here, C(S) refers to C(=S).
As used here, S(O) refers to S(=O).
As used here, $S(O)_2$ refers to $S(=O)_2$.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then 3 hydrogen atoms on the carbon atom can be replaced with substituent groups.

As used herein, "about" in connection with a numerical value means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

The compounds described in the embodiments herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of embodiments the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of embodiments the invention further include hydrates and solvates, as well as anhydrous and non-solvated forms.

The term, "compound," as used herein is meant to include all stereoisomers, geometric iosomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of embodiments the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of embodiments the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

Embodiments of the present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of embodiments the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The compounds of embodiments of the invention can be prepared, for example, according to the reaction pathways, synthetic procedures, and techniques described below.

As shown in Scheme 1, benzaldehyde derivative 1-1 can be reacted with acetaldehyde in the presence of either an acid or a base catalyst to afford cinnamic aldehyde 1-2. Reaction of cinnamic aldehyde 1-2 with an organometallic compound such as a Grignard reagent $R^8MgX^1$ [wherein $X^1$ is halo such as Cl or Br], followed by oxidation of the intermediate alcohol to ketone and by reduction of the C=C bond to a C—C single bond under a hydrogenation condition (for example, in the presence of Pd/C catalyst), affords ketone 1-3. Reaction of ketone 1-3 with amine 1-4 under reductive amination condition (such as in the presence of a borohydride reducing reagent) affords compound 1-5.

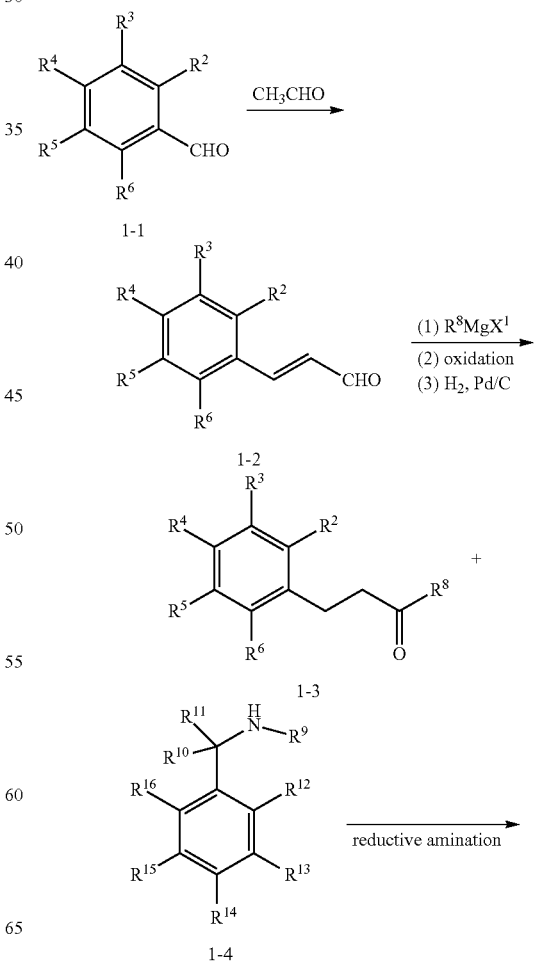

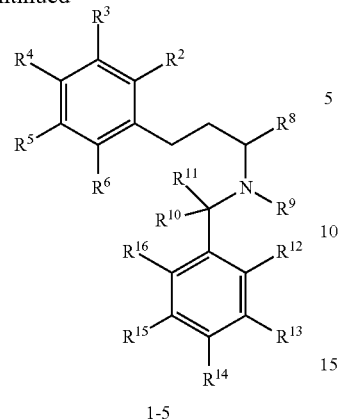

1-5

As shown in Scheme 2, Ketone 2-1 can be reacted with an organometallic compound such as a Grignard reagent $R^7MgX^2$ [wherein $R^7$ can be $C_{1-6}$ alkyl or $C_{3-7}$ cycloalkyl; and $X^2$ can be halo such as Cl or Br] to afford alcohol 2-2a. Reduction of Ketone 2-1 such as in the presence of a borohydride reducing reagent affords alcohol 2-2b. The OH group of alcohol 2-2 (wherein $R^7$ can be H, $C_{1-6}$ alkyl, or $C_{3-7}$ cycloalkyl) can be converted to a better leaving group $Lg^1$ such as OMs [mesylate or $CH_3S(O)_2O$—] or OTf [triflate or $CF_3S(O)_2O$—], followed by reaction with $NH_3$ to afford amine 2-4. Ketone 2-1 can also undergo reductive amination with $NH_3$ to afford amine 2-5.

Scheme 2

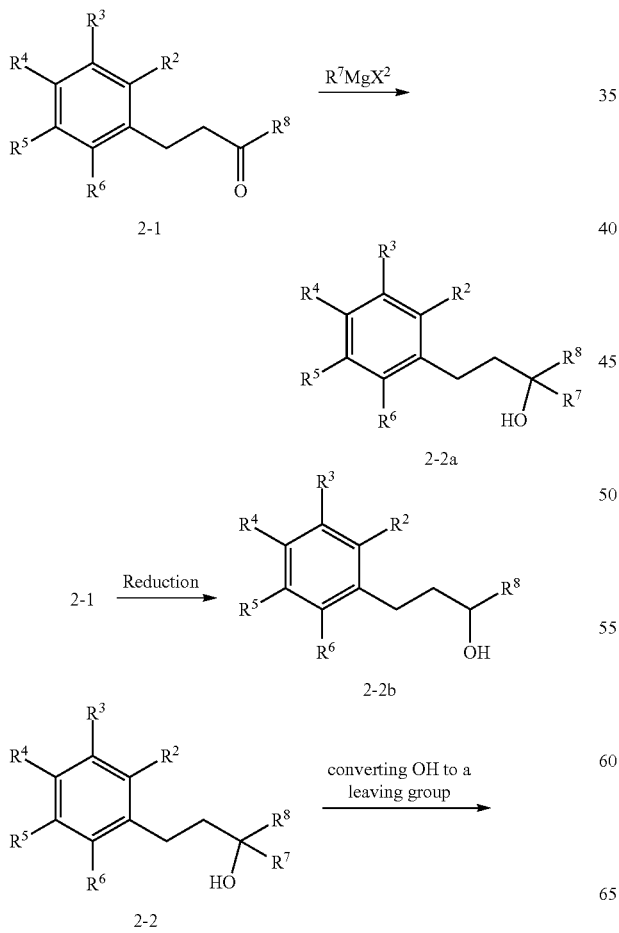

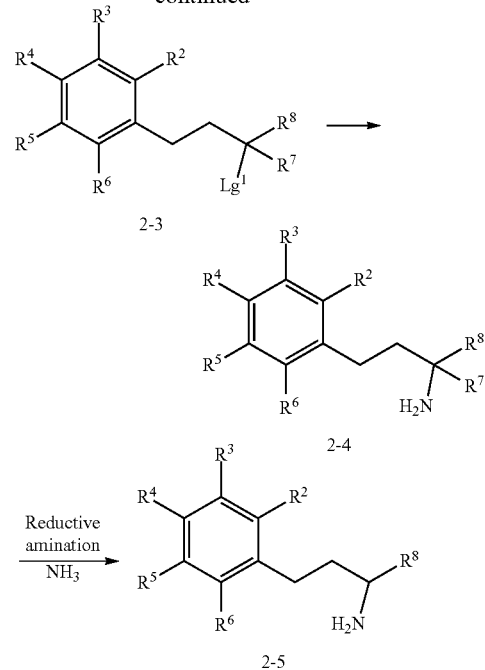

As shown in Scheme 3, amine 3-1 (wherein $R^7$ can be, e.g., H, $C_{1-6}$ alkyl, or $C_{3-7}$ cycloalkyl) can be reacted with compound 3-2 [$Lg^2$ can be a leaving group such as triflate group (-OTf) or halo (e.g. Cl or Br)] to afford compound 3-3.

Scheme 3

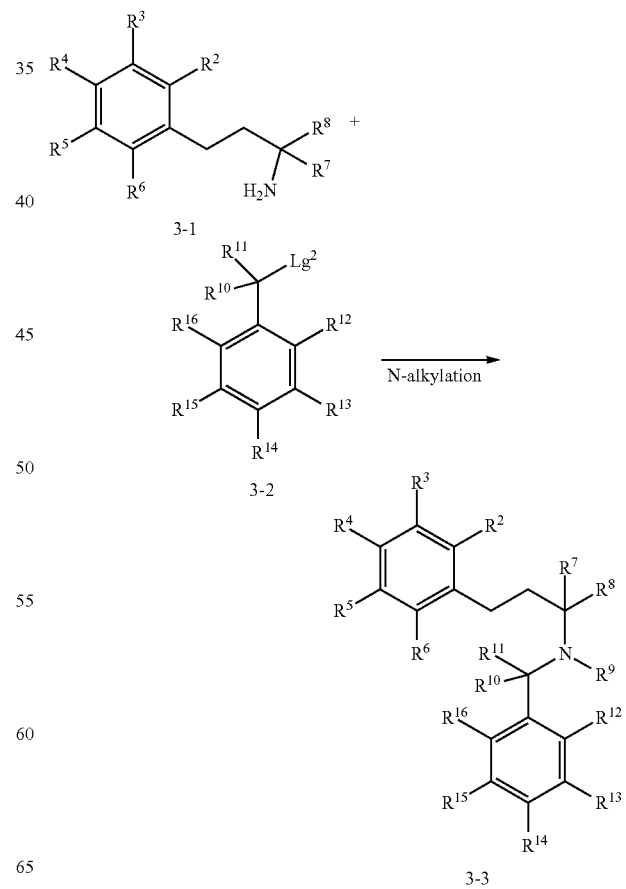

As shown in Scheme 4, benzaldehyde derivative 4-1 can be reacted with a methylmetalic compound such as a Grignard reagent MeMgX$^1$ [wherein X$^1$ is halo such as Cl or Br], followed by oxidation of the intermediate alcohol to ketone to afford ketone 4-2. Ester compound 4-3 [wherein R' can be alkyl (e.g. methyl or ethyl) or arylalkyl; and Pg$^1$ can be an amine protecting group (such as tert-butyloxycarbonyl or Boc; benzyloxycarbonyl or Cbz; or benzyl)] can be reduced to an alcohol (in the presence of a reducing reagent such as Lithium aluminium hydride or LAH), followed by conversion of the OH group to a better leaving group Lg$^3$ such as OMs [mesylate or CH$_3$S(O)$_2$O—] or OTf [triflate or CF$_3$S(O)$_2$O-], to afford compound 4-4.

Reaction of compound 4-2 with compound 4-4 in the presence of a strong base (such as lithium diisopropylamide or LDA), followed by hydrogenation (such as in the presence of a Pd/C catalyst) to reduce the C(O) to CH$_2$ and by removal of the protecting group Pg$^1$ under suitable conditions (for example, a benzyl group can be removed under hydrogenation condition in the presence of Pd/C; or Boc group can be removed under acidic condition), affords amine 4-5. Amine 4-5 can be reacted with compound 4-6 [wherein Lg$^2$ can be a leaving group such as triflate group (-OTf) or halo (e.g. Cl or Br)] to afford compound 4-7.

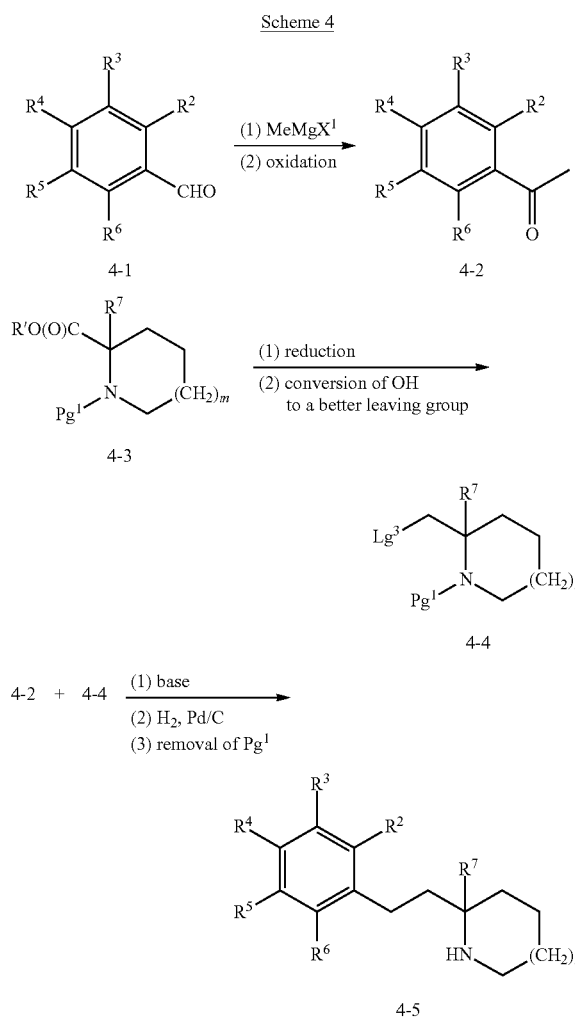

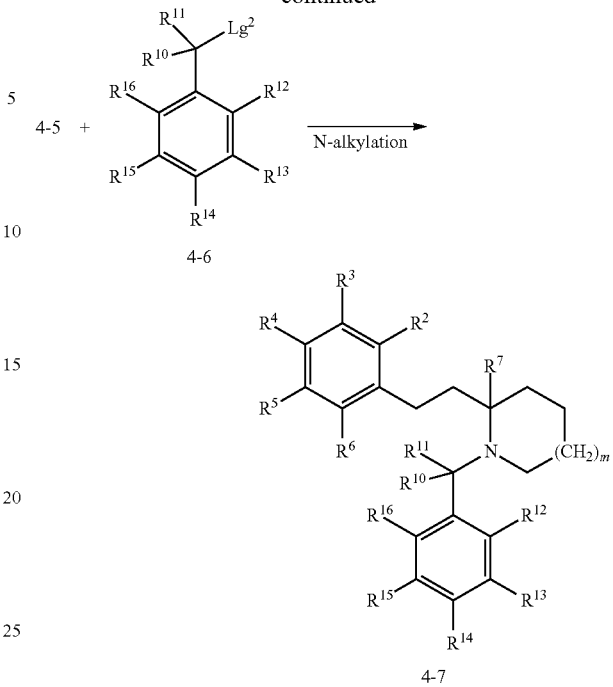

Those skilled in the art can recognize that in all of the schemes described herein, if there are functional (reactive) groups present on a substituent group such as R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)$_2$—. For yet another example, unsaturated bond such as C=C or C≡C can be reduced to saturated bond by hydrogenation. In some embodiments, a primary amine or a secondary amine moiety (present on a substituent group such as R$^1$-R$^{16}$, etc.) can be converted to amide, sulfonamide, urea, or thiourea moiety by reacting it with an appropriate reagent such as an acid chloride, a sulfonyl chloride, an isocyanate, or a thioisocyanate compound. Thus, a compound of Formula I (such as compound 3-3 of Scheme 3) having a substituent which contains a functional group can be converted to another compound of Formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Chemical Conditioning

In some embodiments, a method of preparing an array of chemical compounds from a biological extract such as ginger oil is provided.

The method of the invention, termed "chemical conditioning" is generally applicable to all biological extracts, in particular, natural plant extracts, common or medicinal. See e.g. US20080193574 and WO2008042755, each of which is incorporated herein by reference in its entirety. Chemical conditioning is a method which produces novel unnatural drug-like compounds from readily available natural materials. In general, the "chemical conditioning" of natural extracts coupled with pre-fractionation of the chemically conditioned extracts facilitates successful biochemical screening of extracts by destroying reactive natural compounds that generate false positive results in biochemical assays. Chemical conditioning produces novel lead-like and drug-like compounds and, the reductive amination protocol described here can produce structurally diverse nitrogen-containing products that are particularly lead-like and drug-like.

In certain embodiments of the present invention, a method of preparing chemical compounds from a biological extract is exemplified in Scheme 5a below. According to the method, first, a biological extract, e.g., a plant extract is provided, the biological extract has one or more biological compounds, each biological compound having one or more reactive electrophilic groups. Next, the biological compounds in the biological extract are reacted with an amine to incorporate the amine into the biological compounds. Next, the biological compounds having the incorporated amine are reacted with a reducing agent to reduce the intermediate imine and enamine compounds and form one or more nitrogen-containing chemical compounds. Thus, the resultant nitrogen-containing chemical compounds are derivatives of the biological compounds in the biological extract. In some embodiments, the biological compounds in the biological extract are compounds having ketones and aldehydes that are reacted with various amines. This reaction is followed by hydride reduction of the intermediate imines and enamines to provide secondary and tertiary amines. The reaction of ketones and aldehydes with amines, followed by reduction to form imines and enamines is known in the art.

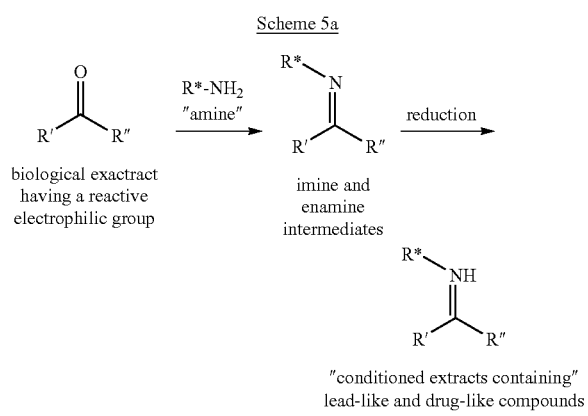

R′ and R″ represent a variety of substituents that make up a biolgical compound; and R* represents a variety of substituent(s) that, together with the nitrogen, make up an amine compound.

The chemical conditioning method described herein employs a biological extract, using many different reagents, to efficiently produce an array of nitrogen-containing chemical compounds. The ready commercial availability of many low molecular weight amines for use as inputs in the reductive amination sequence enables the development of many different and structurally diverse central nervous system druglike mixtures from the same natural extract. Suitable amines for use in the present method are selected from the group consisting of primary amines, secondary amines, cyclic amines, pyrollidine, and amino acids. Suitable reducing agents for use in the present method are selected from the group of hydride reducing agents including but not limited to sodium borohydride, sodium triacetoxyborohydride, and lithium aluminum hydride.

The method may further comprise quenching the reaction a quenching agent, wherein the quenching agent is selected from but not limited to the group consisting of sodium bicarbonate, sodium carbonate, sodium sulfate, sodium sulfate decahydrate. The method may also further comprise isolating one or more of the nitrogen-containing chemical compounds, in a purified or unpurified form. The resultant nitrogen-containing chemical may then be screened or tested for biological activity.

The process of chemical conditioning by reductive amination described herein destroys reactive electrophiles in the natural extract, including ketones, as in the gingerols, and converts them to chemically stable compounds such as amines. The resulting conditioned extracts contain both natural compounds and novel unnatural nitrogen-containing amine products that are potential drug candidates. In the case of the extracts of gingerol, the nitrogen-containing amine products are potential central nervous system drugs.

For the purpose of this disclosure, the following terms have the following meanings.

The term "biological compound" as used herein refers to a chemical compound that occurs in nature.

The term "biological extract" as used herein refers to an extract from a biological sample, such as a plant extract, or other extract from organic matter, containing chemical compounds that occur in nature.

The term "reactive electrophilic group" as used herein refers to an atom or group of atoms that has the ability to react with a nucleophile.

The term "nitrogen-containing derivative" as used herein represents those derivatives containing a nitrogen atom, where the nitrogen atom is a substitution another atom, such as oxygen in the parent compound.

In one embodiment, a specific example of the chemical conditioning process is shown in Scheme 5 below. Scheme 5 shows the two-step reductive amination chemical conditioning protocol performed on ginger oil and ginger oleoresin in accordance with one embodiment of the method, wherein ginger oil or gingerol comprising ketone 5-1 are converted to amine 5-4. According to the method shown in Scheme 5, ginger oil (an extract of ginger containing ketone 5-1 and other molecules occurring in natural ginger) is reacted with amine 5-2 to form compound 5-3. Then, the resultant compound 5-3 is then reduced, with a reducing agent such as a borohydride, to from the nitrogen-containing compound 5-4 (the reaction crude product also include other chemical compounds).

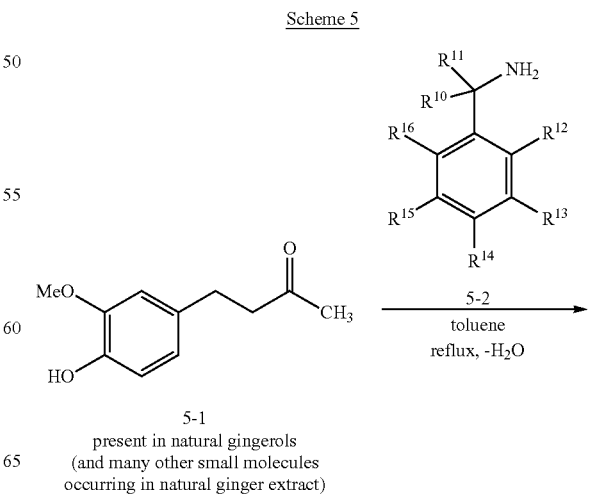

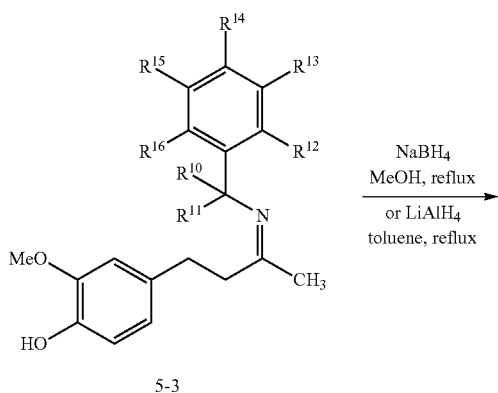

5-3

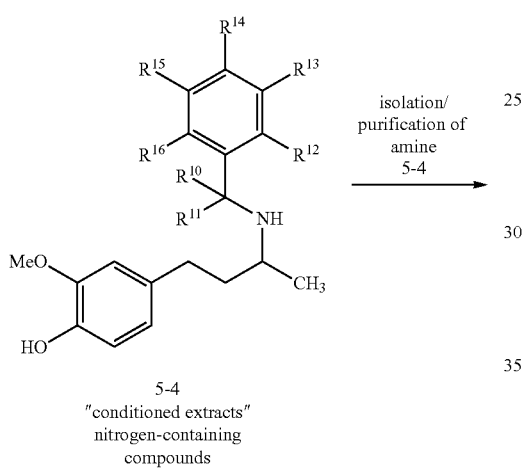

5-4
"conditioned extracts"
nitrogen-containing
compounds

In the next step of the method, amine 5-4 is isolated/purified from the extract (the crude reaction product of the 2-step reductive amination). The conditioned extracts can be fractionated by flash chromatography. The fraction that contains amine 5-4 can undergo further purification/isolation according to the methods known to those in the art. Further isolation and characterization of the fraction that contains amine 5-4 may follow. The isolated amine 5-4 is tested for its biological activity such as by those methods described hereinwith.

Some examples of benzylamine 5-2 used in the chemical conditioning process of the invention shown in Scheme 5 include:

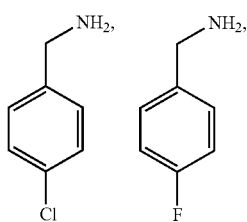

New lead compounds generated by this chemical conditioning method can also be prepared to the synthetic methods described hereinwith.

In some embodiments, the derivatives of ginger oil such as amine 5-4 possess beta-secretase inhibitory activity, and/or inhibit amyloid production, amyloid assembly, the activity/effect of Abeta oligomers on neurons (such as neurons in the brain), amyloid aggregation, amyloid (including amyloid oligomer) binding, or amyloid deposition. These compounds are useful therapeutic agents for the treatment and prevention of cognitive decline, amyloid production, neurodegeneration, and Alzheimer's disease.

Methods

In some embodiments, the compounds of present invention inhibit, treat, or abate (partially inhibit) binding of amyloid (including Abeta oligomers) to neurons (such as neurons in the brain) and are useful for the inhibition, treatment, and abatement of cognitive decline and/or Alzheimer's disease. In some embodiments, the compounds of present invention inhibit, treat, or abate (partially inhibit) one or more of amyloid aggregation, amyloid oligomer binding, and amyloid deposition. In some embodiments, the compounds of present invention inhibit, treat, or abate (partially inhibit) amyloid deposition. In some embodiments, the compounds of present invention inhibit, treat, or abate (partially inhibit) the activity/effect of Abeta oligomers on neurons (such as neurons in the brain) and are useful for the inhibition, treatment, and abatement of cognitive decline and/or Alzheimer's disease. In some embodiments, the compounds of present invention inhibit, treat, or abate (partially inhibit) the activity/effect of Abeta oligomers on neurons (such as neurons in the brain) via disruption of Abeta oligomers, inhibition of Abeta oligomer binding to neurons, and/or counteraction of signal transduction mechanisms of action initiated by Abeta oligomer binding.

In some embodiments, the compounds show activity in a beta-secretase assay and are useful for the inhibition, treatment, and abatement of cognitive decline and Alzheimer's disease. In some embodiments the derivative of ginger oil is a compound in purified and isolated form (for example, with a purity of greater than 80%, 85%, 90%, 95%, 98%, or 99% by weight). The compounds and methods described herein may be used to treat one or more symptoms of cognitive decline and/or Alzheimer's disease such as memory loss, confusion, impaired judgment, personality changes, disorientation, and loss of language skills. Further, the compounds and methods described herein may be useful in inhibiting, treating, and/or abating cognitive decline and/or Alzheimer's disease by restoring long term potentiation, and/or inhibiting, treating, or abatement of one or both of neurodegeneration and general amyloidosis, more specifically, by inhibiting, treating, or abatement of one or more of amyloid production, amyloid assembly, amyloid aggregation, amyloid (including amyloid oligomer) binding, and amyloid deposition.

In some embodiments, compounds of the invention can inhibit, treat, or abate one or more of amyloid production, amyloid assembly, amyloid aggregation, amyloid oligomer binding, and amyloid deposition. In some embodiments, compounds of the invention can restore long term potentiation, inhibit, treat, or abate one or both of neurodegeneration and general amyloidosis.

In some embodiments, compounds of present invention inhibit, treat, or abate (partially inhibit) one or more of amyloid aggregation, amyloid oligomer binding, and amyloid deposition. In some embodiments, the compounds of present invention inhibit (or partially inhibit) amyloid deposition. In some embodiments, the compounds of present invention inhibit, treat, or abate (partially inhibit) binding of amyloid (including Abeta oligomers) to neurons (such as neurons in the brain). In some embodiments, the compounds of present invention are useful for the inhibition, treatment, and abatement of cognitive decline and/or Alzheimer's disease.

In some embodiments, compounds of the invention can inhibit activity of beta-secretase. In some embodiments, compounds of the invention can be used in methods of inhibiting activity of beta-secretase by contacting the beta-secretase with any one or more of the compounds or compositions described herein.

Another aspect of the present invention pertains to methods of treating cognitive decline and/or Alzheimer's disease in an individual (e.g., patient) by administering to the individual a therapeutically effective amount or dose of a compound of the present invention or a pharmaceutical composition thereof.

Treatment of the diseases/disorders herein includes treating one or more symptoms associated with the diseases/disorders, for example, symptoms of cognitive decline and/or Alzheimer's disease.

As used herein, the term "contacting" refers to the bringing together of indicated moieties in an in vitro system or an in vivo system. For example, "contacting" a beta-secretase or a neuron cell (or a neuron cell in the presence of one or more of beta-amyloid oligomers) with a compound of the invention includes the administration of a compound of the present invention to an individual or patient, such as a human, having a beta-secretase or a neuron cell, as well as, for example, introducing a compound of the invention into a sample containing a cellular or purified preparation containing the a beta-secretase or a neuron cell (or a neuron cell in the presence of one or more of beta-amyloid oligomers).

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting/retarding the disease; for example, inhibiting/retarding a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or completely eliminating/curing the disease. As used herein, treating a disease further includes treating one or more symptoms associated with the disease.

Combination Therapies

In certain embodiments, one or more additional pharmaceutical agents for treatment of cognitive decline and/or Alzheimer's disease can be used in combination with the compounds of the present invention for treatment of cognitive decline and/or Alzheimer's disease. The one or more additional pharmaceutical agents can be administered to a patient simultaneously or sequentially.

Pharmaceutical Formulations and Dosage Forms

In certain embodiments, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Embodiments of this invention also include pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

Embodiments of the present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the radio-labeled compounds will depend on the specific application of that radio-labeled compound. For example, for in vitro receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled compound" is a compound that has incorporated at least one radionuclide. In some embodiments the radionuclide is selected from $^{3}H$, $^{14}C$, $^{125}I$, $^{35}S$ and $^{82}Br$.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a beta-secretase or a neuron cell (or a neuron cell in the presence of one or more of beta-amyloid oligomers) by monitoring its concentration variation when contacting with the beta-secretase or the neuron cell (or the neuron cell in the presence of one or more of beta-amyloid oligomers), through tracking the labeling. For another example, a test compound (labeled) can be evaluated for its ability to reduce binding of another compound which is known to bind to beta-secretase or neuron cell (i.e., standard compound). Accordingly, the ability of a test compound to compete with the standard compound for binding to the beta-secretase or the neuron cell directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

Embodiments of the present invention also includes pharmaceutical kits useful, for example, in the treatment or prevention of cognitive decline and/or Alzheimer's disease which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. Certain compounds of the Examples were found to be inhibit, treat, or abate one or more of amyloid production, amyloid assembly, the activity/effect of Abeta oligomers on neurons (such as neurons in the brain), amyloid aggregation, amyloid oligomer binding, and amyloid deposition according to one or more of the assays provided herein. In some further embodiments, certain compounds of the Examples were found to be inhibit, treat, or abate one or more of the activity/effect of Abeta oligomers on neurons (such as neurons in the brain), amyloid aggregation, amyloid (including amyloid oligomer) binding, and amyloid deposition according to one or more of the assays provided herein.

In some embodiments, the compound of invention has an $IC_{50}$ value of less than 100 μM, 50 μM, 20 μM, 15 μM, 10 μM, 5 μM, 1 μM, 500 nM, 100 nM, 50 nM, or 10 nM with respect to inhibition of one or more of the activity/effect of Abeta oligomers on neurons (such as neurons in the brain), amyloid aggregation, amyloid (including amyloid oligomer) binding, and amyloid deposition. In some embodiments, the compound of invention has an $IC_{50}$ value of less than 100 μM, 50

μM, 20 μM, 15 μM, 10 μM, 5 μM, 1 μM, 500 nM, 100 nM, 50 nM, or 10 nM with respect to inhibition the activity/effect of Abeta oligomers on neurons (such as neurons in the brain).

In some embodiments, percentage inhibition of the compound of invention to one or more of the activity/effect of Abeta oligomers on neurons (such as neurons in the brain), amyloid aggregation, amyloid (including amyloid oligomer) binding, and amyloid deposition was measured at a concentration of from 10 nM to 10 μM. In some embodiments, the percentage inhibition measured is about 1% to about 20%, about 20% to about 50%, about 1% to about 50%, or about 1% to about 80%.

The invention may be appreciated in certain aspects with reference to the following examples, offered by way of illustration, not by way of limitation. Materials, reagents and the like to which reference is made in the following examples are obtainable from commercial sources, unless otherwise noted.

EXAMPLES

Materials And Methods

Ginger Oil

The light oil extract from ginger root was obtained by supercritical $CO_2$ extraction.

Ginger Oleoresin

The heavy remainder oil was obtained following extraction of ginger root by supercritical $CO_2$ extraction.

Example 1 a. Conditioned Extraction of Ginger Oil: Reaction of Ginger Oil with 4-Chlorobenzylamine Followed by Reduction with Sodium Borohydride in Methanol and by Fractioning Using Column Chromatography Ginger oil (10 g) was dissolved in toluene (250 mL) and 4-chlorobenzylamine (3.4 g) was added. The mixture was maintained under an atmosphere of nitrogen and heated at reflux with removal of water by Dean-Stark distillation for 16 hours. At this time the Dean-Stark trap was removed and the reaction mixture was cooled to 0° C. on an ice bath. A solution of sodium borohydride (10 g) in methanol (100 mL) was added portion-wise over 30 minutes with vigorous stirring. When the addition was complete the mixture was heated to reflux for 16 hours. At this time the reaction mixture was cooled to room temperature and poured into saturated aqueous sodium bicarbonate solution (300 mL). The resulting mixture was concentrated by rotary evaporation and the aqueous residue was partitioned between water and chloroform. The chloroform layer was dried over anhydrous sodium sulfate and then filtered and concentrated. The products were then fractionated using silica gel column chromatography employing a gradient from 100% chloroform to chloroform:methanol (5:1). The product was detected in the relatively polar fractions by thin layer chromatography (TLC). Product-containing fractions were combined and concentrated then dried under high vacuum overnight to provide a light brown oil (0.672 g). $^1$H NMR (500 MHz, CDCl$_3$) δ: 7.30-7.24 (m, 4H), 6.81 (d, J=7.8 Hz, 1H), 6.66-6.62 (m, 2H), 4.25 (br s, 2H), 3.82 (s, 3H), 3.82 (d, J=13.2 Hz, 1H), 3.72 (d, J=13.2 Hz, 1H), 2.73 (m, 1H), 2.66-2.51 (m, 1H), 1.86-1.78 (m, 1H), 1.72-1.63 (m, 1H), 1.62-1.51 (m, 1H), 1.17 (d, J=6.3 Hz, 3H). $^{13}$C NMR (125 MHz, CDCl$_3$) δ: 146.6, 143.8, 133.9 132.8, 129.9, 129.7, 128.6, 120.8, 114.5, 110.9, 55.8, 51.9, 50.2, 38.5, 31.9, 31.6, 29.7, 26.9, 22.6, 19.9. Analytic MS(M+H+): m/z 320.2.

$^1$H NMR (500 MHz, CD$_3$OD) δ: 7.10-7.30 (m, 4H), 6.63 (br s, 1H), 6.58 (m, 1H), 6.48 (m, 1H), 3.68 (s, 3H), 3.65 (m, 1H), 3.58 (m, 1H), 2.57 (m, 1H), 2.50 (m, 1H), 2.35 (m, 1H), 1.73 (m, 1H), 1.49 (m, 1H), 1.04 (d, 3H). $^{13}$C NMR (125 MHz, CD$_3$OD) δ: 147.5, 145.3, 137.2, 133.3 132.6, 129.9, 128.1, 120.4, 114.7, 111.6, 54.9, 51.3, 49.2, 37.7, 31.5, 18.0.

The weight ratio of Ginger oil to 4-chlorobenzylamine used in the reductive amination is about 3:1 (from 2.7:1 to 3.3:1). The chemical shift measure by $^1$H NMR may vary, for example, up to 0.2 ppm. The chemical shift measure by $^{13}$H NMR may vary, for example, up to 0.5 ppm. The analytical Mass Spectrum may have an experimental error of +/−0.3.

Purity Determination

The purity of the product was measure by HPLC. The major peak of retention time of 2.22 minutes indicating greater than about 80%, 85%, 90, or 95% of purity. The HPLC conditions used are as follows.

HPLC Conditions:

Mobile Phase A: 13.3 mM ammonium formate/6.7 mM formic acid in water

Mobile Phase B: 6 mM ammonium formate/3 mM formic acid in water/CH$_3$CN (⅕, v/v)

Column: Synergi Fusion-RP 100A Mercury, 2×20 mm, 2.5 micron (Phenomenex Part No 00M-4423-B0_CE)

Gradient Program: RT=2.22 minutes

| Time, minute | % Phase B | Flow rate, ml/min |
| --- | --- | --- |
| 0 | 100 | 0.5 |
| 1 | 100 | 0.5 |
| 2.5 | 40 | 0.5 |
| 3.4 | 40 | 0.5 |
| 3.5 | 100 | 0.5 |
| 4.5 | 100 | 0.5 |

The purity of the product was also measure by $^1$H NMR indicating it to be a single compound of a purity of greater than 90% or 95%.

The structure of Compound Example 1 (or Example Compound 1) is determined to be as follows.

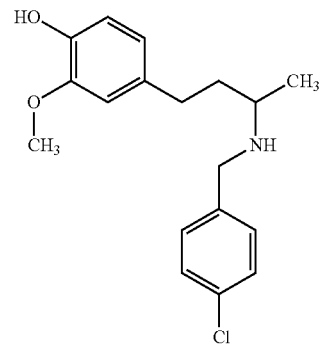 [SMILES: COc1cc(CCC(C)NCc2ccc(Cl)cc2)ccc1O]

Compound Example 1

4-(3-(4-chlorobenzylamino)butyl)-2-methoxyphenol

B. Synthesis by Reductive Amination

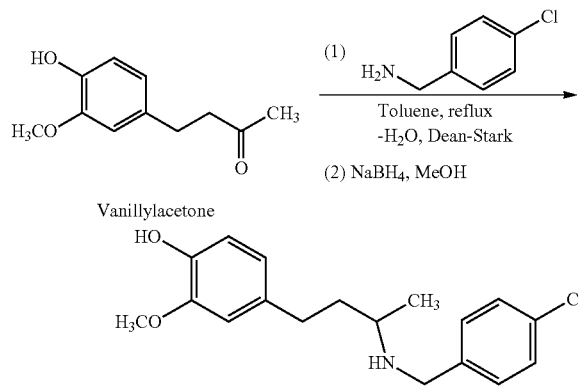

Vanillylacetone (5.00 g, 25.7 mmol) was dissolved in toluene (250 mL) and 4-chlorobenzylamine (3.82 g, 27.0 mmol) was added. The mixture was maintained under an atmosphere of nitrogen and heated at reflux with removal of water by Dean-Stark distillation for 16 hours. At this time the Dean-Stark trap was removed and the reaction mixture was cooled to 0° C. on an ice bath. A solution of sodium borohydride (5 g) in methanol (100 mL) was added portion-wise over 30 minutes with vigorous stirring. When the addition was complete the mixture was heated at reflux for 16 hours. At this time the reaction mixture was cooled to room temperature and poured into saturated aqueous sodium bicarbonate solution (300 mL). The resulting mixture was concentrated by rotary evaporation and the aqueous residue was partitioned between water and chloroform. The chloroform layer was dried over anhydrous sodium sulfate and then filtered and concentrated. The product was then purified using silica gel column chromatography employing a mobile phase of 5% ammonia-methanol in chloroform. Product-containing fractions were combined and concentrated then dried under high vacuum overnight to provide a light brown oil (6.16 g, 75%). $^1$H NMR, $^{13}$C NMR, and Mass Spectrum of the product were substantially the same as those in Example 1, A (made by the Conditioned Extraction method).

Example 2

A. Conditioned Extraction of Ginger Oil: Reaction of Ginger Oil with 4-Trifluoromethylbenzylamine Followed by Reduction with Sodium Borohydride in Methanol and by Fractioning Using Column Chromatography Ginger oil (10 g) was dissolved in toluene (250 mL) and 4-trifluoromethylbenzylamine (3.5 g) was added. The mixture was maintained under an atmosphere of nitrogen and heated at reflux with removal of water by Dean-Stark distillation for 16 hours. At this time the Dean-Stark trap was removed and the reaction mixture was cooled to 0° C. on an ice bath. A solution of sodium borohydride (10 g) in methanol (100 mL) was added portion-wise over 30 minutes with vigorous stirring. When the addition was complete the mixture was heated to reflux for 16 hours. At this time the reaction mixture was cooled to room temperature and poured into saturated aqueous sodium bicarbonate solution (300 mL). The resulting mixture was concentrated by rotary evaporation and the aqueous residue was partitioned between water and chloroform. The chloroform layer was dried over anhydrous sodium sulfate and then filtered and concentrated. The products were then fractionated using silica gel column chromatography employing a gradient from 100% chloroform to chloroform:methanol (5:1). The product was detected in the relatively polar fractions by thin layer chromatography (TLC). Product-containing fractions were combined and concentrated then dried under high vacuum overnight to provide a light brown oil (0.761 g). $^1$H NMR (500 MHz, CDCl$_3$) δ: 7.57 (d, J=7.8 Hz, 2H), 7.43 (d, J=7.9 Hz, 2H), 6.82 (d, J=7.3 Hz, 1H), 6.65 (m, 2H), 5.16-4.42 (br s, 2H), 3.90 (d, J=13.7 Hz, 1H), 3.84 (s, 3H), 3.80 (d, J=13.7 Hz, 1H), 2.76-2.70 (m, 1H), 2.67-2.55 (m, 2H), 1.84-1.77 (m, 1H), 1.69-1.63 (m, 1H), 1.17 (d, J=6.3 Hz, 3H). $^{13}$C NMR (125 MHz, CDCl$_3$) δ: 146.7, 144.6, 143.9, 134.0, 129.1, 128.4, 127.5, 125.4, 125.3, 123.2, 120.8, 114.6, 111.0, 55.7, 52.1, 50.6, 38.8, 32.0, 20.1. MS (CI) m/z 353 (M$^+$).

The weight ratio of ginger oil to 4-trifluoromethylbenzylamine used in the reductive amination is about 3:1 (from 2.7:1 to 3.3:1). The chemical shift measure by $^1$H NMR may vary, for example, up to 0.2 ppm. The chemical shift measure by $^{13}$H NMR may vary, for example, up to 0.5 ppm. The analytical Mass Spectrum may have an experimental error of +/−0.3.

Purity Determination

The purity of the product was measure by HPLC. The major peak of retention time of 2.22 minutes indicating greater than about 80%, 85%, 90, or 95% of purity. The HPLC conditions used are as follows.

HPLC Conditions:

Mobile Phase A: 13.3 mM ammonium formate/6.7 mM formic acid in water Mobile Phase B: 6 mM ammonium formate/3 mM formic acid in water/CH$_3$CN (1/9, v/v)

Column: Synergi Fusion-RP 100A Mercury, 2×20 mm, 2.5 micron (Phenomenex Part No 00M-4423-B0_CE)

Gradient Program: RT=2.22 minutes

| Time, minute | % Phase B | Flow rate, ml/min |
|---|---|---|
| 0 | 100 | 0.5 |
| 1 | 100 | 0.5 |
| 2.5 | 40 | 0.5 |
| 3.4 | 40 | 0.5 |
| 3.5 | 100 | 0.5 |
| 4.5 | 100 | 0.5 |

The purity of the product was also measure by $^1$H NMR indicating it to be a single compound of a purity of greater than 90% or 95%.

The structure of Compound Example 2 (or Example Compound 2) is determined to be as follows.

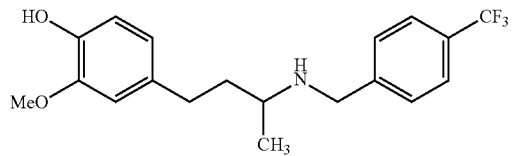 [SMILES: COc1cc(CCC(C)NCc2ccc(C(F)(F)F)cc2)ccc1O]

Compound Example 2

4-(3-(4-(trifluoromethyl)benzylamino)butyl)-2-methoxyphenol

B. Synthesis by Reductive Amination

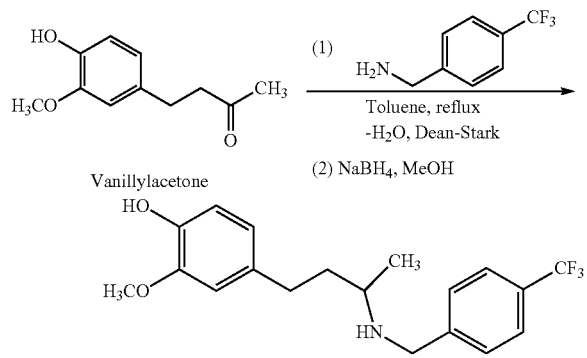

Vanillylacetone (5.00 g, 25.7 mmol) was dissolved in toluene (250 mL) and 4-trifluoromethylbenzylamine (4.73 g, 27.0 mmol) was added. The mixture was maintained under an atmosphere of nitrogen and heated at reflux with removal of water by Dean-Stark distillation for 16 hours. At this time the Dean-Stark trap was removed and the reaction mixture was cooled to 0° C. on an ice bath. A solution of sodium borohydride (5 g) in methanol (100 mL) was added portion-wise over 30 minutes with vigorous stirring. When the addition was complete the mixture was heated at reflux for 16 hours. At this time the reaction mixture was cooled to room temperature and poured into saturated aqueous sodium bicarbonate solution (300 mL). The resulting mixture was concentrated by rotary evaporation and the aqueous residue was partitioned between water and chloroform. The chloroform layer was dried over anhydrous sodium sulfate and then filtered and concentrated. The product was then purified using silica gel column chromatography employing a mobile phase of 5% ammonia-methanol in chloroform. Product-containing fractions were combined and concentrated then dried under high vacuum overnight to provide a light brown oil (6.72 g, 74%). $^1$H NMR, $^{13}$C NMR, and Mass Spectrum of the product were substantially the same as those in Example 2, A (made by the Conditioned Extraction method).

Example AA

Exocytosis Assay/MTT Assay

Primary neurons from E18 Sprague-Dawley rat embryos are plated at optimized concentrations in 384 well plates in NB media (Invitrogen). Neurons are maintained in cultures for 3 weeks, with twice weekly feeding of NB media with $N_2$ supplement (Invitrogen). A test compound is added to cells, followed by addition of Vehicle or Abeta oligomer preparations (1.5 μM), and incubated for 1 to 24 hr at 37° C. in 5% $CO_2$. MTT reagent (3-(4,5-dimethylthizaol-2yl)-2,5diphenyl tetrazolium bromide) (Roche Molecular Biochemicals) is reconstituted in phosphate buffered saline to 5 mg/mL. 10 μL of MTT labeling reagent is added to each well and incubated at 37° C. for 1 h, then imaged.

Each assay plate is formatted so that compounds are tested with and without Abeta on each plate. This design eliminates toxic or metabolically active compounds early on in the screening cascade (at the level of the primary screen). Statistical performance of the screening plate layout are assessed, screening will be initiated if the current performance is maintained.

Similar procedures for exocytosis assays/MTT assays can be found in the literature. See e.g., Liu Y, et. al., Detecting bioactive amyloid beta peptide species in Alzheimer's disease. J Neurochem. 2004 November; 91(3):648-56; Liu Y, and Schubert D. "Cytotoxic amyloid peptides inhibit cellular 3-(4,5-dimethylthiazol-2-yl)-2,5-diphenyltetrazolium bromide (MTT) reduction by enhancing MTT formazan exocytosis." J Neurochem. 1997 December; 69(6):2285-93; and Liu Y, and Schubert D. "Treating Alzheimer's disease by inactivating bioactive amyloid beta peptide" Curr. Alzheimer Res. 2006 April; 3(2):129-35.

Experimental Controls:

Abeta 1-42 oligomers made according to published methods methods [See e.g. Dahlgren et al., "Oligomeric and fibrillar species of amyloid-beta peptides differentially affect neuronal viability" J Biol Chem. 2002 Aug. 30; 277(35):32046-53. Epub 2002 Jun. 10.; LeVine H 3rd. "Alzheimer's beta-peptide oligomer formation at physiologic concentrations" Anal Biochem. 2004 Dec. 1; 335(1):81-90; Shrestha et. al, "Amyloid beta peptide adversely affects spine number and motility in hippocampal neurons" Mol Cell Neurosci. 2006 November; 33(3):274-82. Epub 2006 Sep. 8; Puzzo et al., "Amyloid-beta peptide inhibits activation of the nitric oxide/cGMP/cAMP-responsive element-binding protein pathway during hippocampal synaptic plasticity" J Neurosci. 2005 Jul. 20; 25(29):6887-97; Barghorn et al., "Globular amyloid beta-peptide oligomer—a homogenous and stable neuropathological protein in Alzheimer's disease" J Neurochem. 2005 November; 95(3):834-47. Epub 2005 Aug. 31; Johansson et al., Physiochemical characterization of the Alzheimer's disease-related peptides A beta 1-42 Arctic and A beta 1-42 wt. FEBS J. 2006 June; 2 73(12):2618-30] as well as brain-derived Abeta oligomers (See e.g. Walsh et al., Naturally secreted oligomers of amyloid beta protein potently inhibit hippocampal long-term potentiation in vivo. Nature (2002). 416, 535-539; Lesne et al., A specific amyloid-beta protein assembly in the brain impairs memory. Nature. 2006 Mar. 16; 440(7082):352-7; Shankar et al, Amyloid-beta protein dimers isolated directly from Alzheimer's brains impair synaptic plasticity and memory. Nat Med. 2008 August; 14(8):837-42. Epub 2008 Jun. 22) constitute the positive controls. Negative controls include vehicle-treated neurons as well as neurons treated with 28 μM concentrations of memantine. Memantine produces 50% inhibition of oligomer effects at this dose. These controls, on each plate, serve as normalization tools to calibrate assay performance on a plate-by-plate basis.

Primary Neuronal Cultures

Optimal cell density is determined based on cellular response to Abeta oligomers using the exocytosis assay as a readout, and immunohistochemical analysis of the relative proportion of glia to neurons in the cultures. Cultures are monitored on a weekly basis with immunohistochemistry and image processing-based quantification to monitor the percentage of the cultures that are neurons vs. glia (Glial cells). Cultures containing more than 20% glia (positive for GFAP) vs. neurons (staining positively with antibodies directed against MAP2) at the screening age of 21 days in vitro (21 DIV) are rejected.

Abeta Oligomer Preparations

Human amyloid peptide 1-42 is obtained from California Peptide, with lot-choice contingent upon quality control analysis. Quality controls of oligomer preparations consist of Westerns to determine oligomer size ranges and relative concentrations, and the MTT assay to confirm exocytosis acceleration without toxicity. Toxicity is monitored in each image-based assay via quantification of nuclear morphology visualized with the DNA binding dye DAPI (Invitrogen). Nuclei that are fragmented are considered to be in late stage apoptosis (Majno and Joris '95). Peptide lots producing unusual peptide size ranges or significant toxicity at a standard 1.5 uM concentration on neurons are rejected. Plate-based controls—The assay optimization will be complete when reformatted plates achieve a minimum of statistically significant two-fold separation between vehicle and Abeta oligomer-treated neurons (p<0.01, Student's t-test, unequal variance) on a routine basis, with no more than 10% CV between plates, equivalent to its current performance.

Statistical Software and Analysis:

Data handling and analysis are accomplished by Cellomics VTI image analysis software and STORE automated database software. Because of the low dynamic range and neuronal well-to-well variability after three weeks in culture, statistical comparisons are made via pairwise Tukey-Kramer analysis to determine the significance of the separation between compound+Abeta oligomers from Abeta alone, and between compound alone from vehicle.

These statistics are more akin to what is seen in animal behavioral testing than the z' statistic that has been used for the past two decades in high throughput screening. The ability of mature primary neurons to more closely approximate the electrophysiologically mediated signal transduction network of the adult brain justifies this screening strategy. Power analysis will be set for a number of replicate screening wells that will minimize false negatives (e.g N=4) and shift the burden of distinguishing false positives from actual hits to dose-response confirmation screening. Rank ordering of compounds is done on the basis of secondary assay mechanism of action and physicochemical properties of the compound structures. Certain test compounds significantly reverse the effects of Abeta oligomers but not affect neuronal metabolism.

Compound Example 1 was dosed in the MTT assay and was shown to block the Abeta oligomer-induced acceleration of exocytosis with an $EC_{50}$ of 10 µM, indicating that Compound Example 1 blocks/abate the activity/effect of Abeta oligomer on neuron cells.

Example BB

Binding Assay

Each test compound was added to a plate followed by an addition of one or more of Abeta 1-42 Oligomers. The plates were fixed with 3.7% paraformaldehyde in phosphate buffered saline (PBS) for 15 min. The plate was then washed 3× with PBS for 5 min each. The plates were blocked at room temperature for 1 hour in 5% goat serum and 0.5% Triton X-100 (CAS number: 9002-93-1) in PBS. Primary antibodies (anti-MAP 2 polyclonal, Millipore #AB5622 and anti-Beta Amyloid 6E10 monoclonal, Convance #SIG-39300) were diluted 1:1000 in 5% goat serum with PBS. Primary antibodies were incubated either overnight at 4° C. or 1 hour at RT. The plate was then washed 3× with PBS for 5 min each. Secondary antibodies (Alex Flor 488 polyclonal, Invitrogen #A11008 and Alexa Flor 647 monoclonal, Invitrogen #A21235) were diluted 1:1000 in 5% goat serum with PBS. Secondary antibodies were incubated at RT for 1 hr. The plates were washed once with PBS. DAPI (4',6-diamidino-2-phenylindole, Invitrogen) was then applied at 0.03 µg/µL and incubated at RT for 5 min, then washed with PBS. Image process was carried out for analysis.

Similar procedures for binding assays can be found in the literature. See e.g., Look G C, et. al. Discovery of ADDL—targeting small molecule drugs for Alzheimer's disease. Curr Alzheimer Res. 2007 December; 4(5):562-7. Review.

Abeta Oligomer Preparations:

Human amyloid peptide 1-42 is obtained from California Peptide, with lot-choice contingent upon quality control analysis. Abeta 1-42 oligomers made according to published methods [See e.g. Dahlgren et al., "Oligomeric and fibrillar species of amyloid-beta peptides differentially affect neuronal viability" J Biol Chem. 2002 Aug. 30; 277(35):32046-53. Epub 2002 Jun. 10.; LeVine H 3rd. "Alzheimer's beta-peptide oligomer formation at physiologic concentrations" Anal Biochem. 2004 Dec. 1; 335(1):81-90; Shrestha et. al, "Amyloid beta peptide adversely affects spine number and motility in hippocampal neurons" Mol Cell Neurosci. 2006 November; 33(3):274-82. Epub 2006 Sep. 8; Puzzo et al., "Amyloid-beta peptide inhibits activation of the nitric oxide/cGMP/cAMP-responsive element-binding protein pathway during hippocampal synaptic plasticity" J Neurosci. 2005 Jul. 20; 25(29):6887-97; Barghorn et al., "Globular amyloid beta-peptide oligomer—a homogenous and stable neuropathological protein in Alzheimer's disease" J Neurochem. 2005 November; 95(3):834-47. Epub 2005 Aug. 31; Johansson et al., Physiochemical characterization of the Alzheimer's disease-related peptides A beta 1-42 Arctic and A beta 1-42 wt. FEBS J. 2006 June; 2 73(12):2618-30] as well as brain-derived Abeta oligomers (See e.g. Walsh et al., Naturally secreted oligomers of amyloid beta protein potently inhibit hippocampal long-term potentiation in vivo. Nature (2002). 416, 535-539; Lesne et al., A specific amyloid-beta protein assembly in the brain impairs memory. Nature. 2006 Mar. 16; 440(7082):352-7; Shankar et al, Amyloid-beta protein dimers isolated directly from Alzheimer's brains impair synaptic plasticity and memory. Nat Med. 2008 August; 14(8):837-42. Epub 2008 Jun. 22) will serve as positive controls. Quality controls of oligomer preparations consist of Westerns to determine oligomer size ranges and relative concentrations, and the MTT assay to confirm exocytosis acceleration without toxicity. Toxicity is monitored in each image-based assay via quantification of nuclear morphology visualized with the DNA binding dye DAPI (Invitrogen). Nuclei that are fragmented are considered to be in late stage apoptosis (Majno and Joris Apoptosis, oncosis, and necrosis. An overview of cell death. Am J Pathol 1995; 146:3-16). Peptide lots producing unusual peptide size ranges or significant toxicity at standard concentrations on neurons are rejected.

Image Processing

Images were captured and analyzed with the Cellomics VTI automated microscope platform, using the Neuronal Profiling algorithm. For statistical analysis, a Tukey-Kramer pair-wise comparison with unequal variance was used.

Western Blots

Samples containing Abeta 1-42 were diluted (1:5) in non-reducing lane marker sample buffer (Pierce #1859594). A 30 microliter (µL) sample was loaded onto an eighteen well precast 4-15% Tris-HCl gel (BIORAD #345-0028). Electrophoresis was performed in a BIO-RAD Criterian precast gel system using Tris-Glycine buffer at 125 volt (V) for 90 minutes. The gels were blotted onto 0.2 µM nitrocellulose membranes in Tris-Glycine/10% methanol buffer at 30V for 120 minutes. The membranes were boiled for 5 minutes in a PBS solution and blocked over night with TBS/5% milk solution at 4° C. The membrane was probed with 6E10-HRP (Covance #SIG-39345) diluted to 10 µg/mL in TBS/1% milk solution for one hour at room temperature. Membrane was washed three times for 40 minutes each with a solution of TBS/0.05% tween-20 and developed with ECL reagent (BIO-RAD #162-0112) for 5 minutes. Image acquisition was performed on an Alpha Innotech FluorChem Q quantitative imaging system and analyzed with AlphaView Q software.

PK studies:

PK studies are performed at CEREP Inc of Redmond Wash., according to their standard protocols: The plasma samples were processed using acetonitrile precipitation and analyzed by HPLC-MS or HPLC-MS/MS. Peak areas were recorded, and the concentrations of the test compound in the unknown plasma samples were determined using the respective calibration curve. The reportable linear range of the assay was determined, along with the lower limit of quantitation (LLQ).

NMR Spectroscopy and Mass Spectrometry:

Active fractions were analyzed by 1H NMR (Varian 500 MHz NMR spectrometer) and purified compounds were characterized using a combination 1D and 2D 1H NMR experiments and 13C NMR experiments. Structure proof was obtained using these NMR techniques in combination with low resolution mass spectrometry to determine molecular weight and high resolution mass spectrometry (Thermo Finnigan LCQ Ion trap) to determine composition-of-matter.

Compound Example 1 was shown to partially block binding of the Abeta oligomer ligand to neurons by 24% according to the binding assay (using imaging processing algorithm).

Example CC

Pharmacokinetic Studies

Pharmacokinetic studies were performed according to the following protocols: The plasma samples were processed using acetonitrile precipitation and analyzed by HPLC-MS or HPLC-MS/MS. Peak areas were recorded, and the concentrations of the test compound in the unknown plasma samples were determined using the respective calibration curve. The reportable linear range of the assay was determined, along with the lower limit of quantitation (LLQ). For example, Compound Example 1 was determined to have a half life of 46 minutes in the plasma of rats when injected intravenously at 1 mg/Kg.

Example DD

A Primary Neuron-Based Functional Screening Assay to Detect Small Molecule Abeta Oligomer Blockers Primary rat neurons grown for at least 3 weeks in vitro were chosen as the basis for this screening assay. These neurons express the full complement of synaptic proteins characteristic of neurons in the mature brain, and exhibit a complex network of activity-dependent electrical signaling. Neurons and glia in such cultures have molecular signaling networks exhibiting excellent registration with intact brain circuitry, and for this reason have been used for over two decades as a model system for learning and memory (See e.g. Kaech S, Banker G. Culturing hippocampal neurons. Nat Protoc. 2006; 1(5):2406-15. Epub 2007 Jan. 11; See also Craig A M, Graf E R, Linhoff M W. How to build a central synapse: clues from cell culture. Trends Neurosci. 2006 January; 29(1):8-20. Epub 2005 Dec. 7. Review). More complex systems such as acute or organotypic brain slices are very useful but not amenable to high throughput screening. Immortalized or transformed neuronal cell lines are amenable to high throughput screening, but do not replicate the electrophysiological state-dependent signaling of primary neuronal cultures and are unlikely to adequately model the subtle alterations in this signaling that are caused by oligomers during the earliest manifestations of the disease state (See e.g. Görtz P, Fleischer W, Rosenbaum C, Otto F, Siebler M. Neuronal network properties of human teratocarcinoma cell line-derived neurons. Brain Res. 2004 Aug. 20; 1018(1):18-25). For this reason, primary neuronal cultures were chosen because of their ability to be used in high throughput screens and fidelity to what occurs in vivo.

Reduced formazan was first visible in intracellular vesicles (FIG. 1A). Example of neurons filled with labeled vesicles following endocytosis of dye and reduction to an insoluble purple product. (Scale bar=20 microns in FIG. 1A). Eventual formazan exocytosis was accelerated via Abeta oligomers in mature hippocampal neurons in vitro (FIG. 1B). Example photomicrograph of neurons covered with insoluble purple dye that have been extruded via exocytosis. The dye precipitated in the aqueous environment of the culture and formed needle-shaped crystals on the surface of the neuron. (FIG. 1B). Endocytosis rate was altered in the presence of Abeta oligomers. (FIG. 1C) Exocytosis rate was altered in the presence of Abeta oligomers (FIG. 1D).

Since synaptic and memory deficits, and not widespread cell death, predominate at the earliest stages of Alzheimer's disease, assays that measure these changes can be used to discover small molecule inhibitors of oligomer activity. The MTT assay can be used as a measure of toxicity in cultures. Yellow tetrazolium salts were endocytosed by cells and reduced to insoluble purple formazan in the endosomal pathway. The level of purple formazan was a reflection of the number of actively metabolizing cells in culture, and reduction in the amount of formazan was taken as a measure of cell death or metabolic toxicity in culture. When observed through a microscope, the purple formazan was first visible in intracellular vesicles that fill the cell (FIG. 1A). Over time, the vesicles were exocytosed and the formazan precipitated as needle-shaped crystals on the outer surface of the plasma membrane as the insoluble formazan was exposed to the aqueous media environment (FIG. 1B). Cells respond to sublethal levels of Abeta oligomers by selectively accelerating the exocytosis rate of reduced formazan, while leaving endocytosis rate unaffected, which can be seen in mature primary neurons in vitro and quantified these morphological shifts via automated microscopy and image processing. At a given point in time following tetrazolium salt addition to the culture well, vehicle-treated cells had the appearance of those in FIG. 1A, while Abeta oligomer-treated cells had the appearance of those in FIG. 1B. Under these circumstances, there was no overall change in the total amount of reduced formazan, simply a shift in its morphology. This assay is sensitive to low levels of oligomers that do not cause cell death.

Evidence suggests that Abeta oligomer-mediated reduction in neuronal surface receptor expression mediated by membrane trafficking are the basis for oligomer inhibition of electrophysiological measures of synaptic plasticity (LTP) and thus learning and memory (See Kamenetz F, Tomita T, Hsieh H, Seabrook G, Borchelt D, Iwatsubo T, Sisodia S, Malinow R. APP processing and synaptic function. Neuron. 2003 Mar. 27; 37(6):925-37; and Hsieh H, Boehm J, Sato C, Iwatsubo T, Tomita T, Sisodia S, Malinow R. AMPAR removal underlies Abeta-induced synaptic depression and dendritic spine loss. Neuron. 2006 Dec. 7; 52(5):831-43). Measuring membrane trafficking rate changes induced by oligomers via formazan morphological shifts has been used in cell lines to discover Abeta oligomer-blocking drugs [Maezawa I, Hong H S, Wu H C, Battina S K, Rana S, Iwamoto T, Radke G A, Pettersson E, Martin G M, Hua D H, Jin L W. A novel tricyclic pyrone compound ameliorates cell death associated with intracellular amyloid-beta oligomeric complexes. J Neurochem. 2006 July; 98(1):57-67; Liu Y, Schubert D. Cytotoxic amyloid peptides inhibit cellular 3-(4, 5-dimethylthiazol-2-yl)-2,5-diphenyltetrazolium bromide (MTT) reduction by enhancing MTT formazan exocytosis. J Neurochem. 1997 December; 69(6):2285-93; Liu Y, Dargusch R, Banh C, Miller C A, Schubert D. Detecting bioactive amyloid beta peptide species in Alzheimer's disease. J Neurochem. 2004 November; 91(3):648-56; Liu Y, Schubert D. Treating Alzheimer's disease by inactivating bioactive amyloid beta peptide. Curr Alzheimer Res. 2006 April; 3(2):129-35; Rana S, Hong H S, Barrigan L, Jin L W, Hua D H. Syntheses of tricyclic pyrones and pyridinones and protection of Abeta-peptide induced MC65 neuronal cell death. Bioorg Med Chem Lett. 2009 Feb. 1; 19(3):670-4. Epub 2008 Dec. 24; and Hong H S, Maezawa I, Budamagunta M, Rana S, Shi A, Vassar R, Liu R, Lam K S, Cheng R H, Hua D H, Voss J C, Jin L W. Candidate anti-Abeta fluorene compounds selected from analogs of amyloid imaging agents. Neurobiol Aging. 2008 Nov. 18. (Epub ahead of print)] that lower Abeta brain levels in rodents in vivo [Hong H S, Rana S, Barrigan L, Shi A, Zhang Y, Zhou F, Jin L W, Hua D H. Inhibition of Alzheimer's amyloid toxicity with a tricyclic pyrone molecule in vitro and in vivo. J Neurochem. 2009 February; 108(4):1097-1108].

The exocytosis assay was adapted for use with mature primary neuronal cultures grown for 3 weeks in vitro. Abeta oligomers caused a dose-dependent decrease in the amount of intracellular vesicles (puncta) filled with reduced purple formazan (FIG. 2A, squares; 3 µM dose corresponds to image in FIG. 2C) as measured via image processing using a Cellomics VTI automated microscopy system. Increasing the amount of Abeta oligomers eventually resulted in overt toxicity. Thus, the concentration of neuroactive Abeta oligomers was much lower than that causing cell death. This decrease can be blocked by adding stoichiometric amounts of anti-Abeta monoclonal antibody 6E10 (IgG) to the cultures prior to oligomer addition (FIG. 2A, circle; the circle corresponds to image in FIG. 2D; antibody alone [down triangle] has no effect on the neurons). Several compounds were tested that have been reported to block the effects of Abeta oligomers, including the sugar alcohol scyllo-inositol (AZD-103), the nAChR antagonist hexamethonium bromide, and the NMDAR antagonists MK-801 and none were active (Fenili et al., '07, Calabrese et al., '06, LeCor et al., '07).

The assay was optimized for performance in 384-well microtiter plates with automated liquid handling robotics for compound formatting and assay plate stamping, routinely achieving statistically significant two-fold separation between vehicle and Abeta oligomer-treated neurons (Student's t-test, unequal variance). Compounds were added to neurons first, then oligomers were added. When configured in this manner the assay was able to detect compounds that act via disruption of oligomers, inhibition of oligomer binding to neurons, or counteraction of signal transduction mechanisms of action initiated by oligomer binding.

Figure 2:
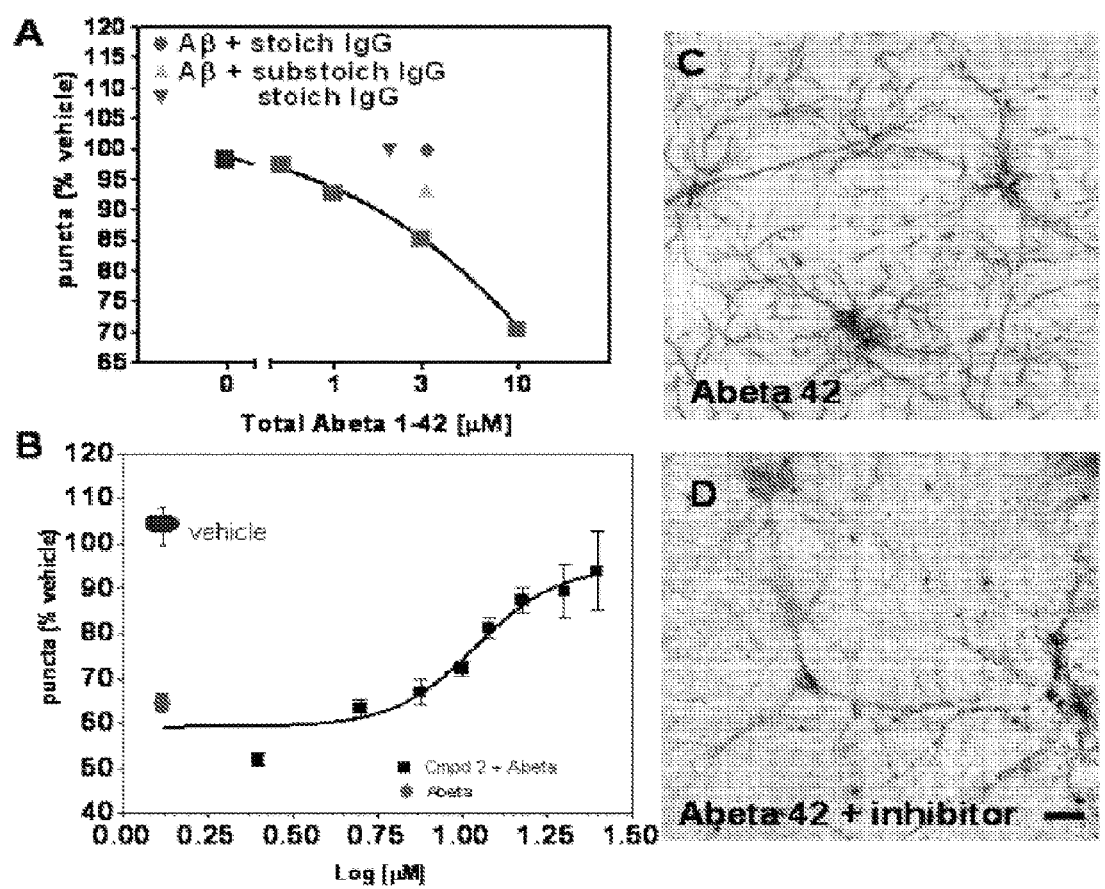
FIG. 2 shows inhibition of processed product of amyloid precursor protein-mediated membrane trafficking effect by Compound Example 2.

Compounds were considered active if they significantly block Abeta-mediated changes in membrane trafficking, but do not significantly affect membrane trafficking when dosed on their own. An example is shown in FIG. 2B; Compound Example 2 inhibits oligomer effects on membrane trafficking with an EC50 of 7 µM.

FIG. 2A shows dose-dependent decrease of intracellular formazan-filled vesicles (puncta) caused by Abeta 42 oligomer treatment acceleration of exocytosis (squares). Oligomer effects were blocked by anti Abeta IgG (circle and up triangle; circle refers to stoich amount of IgG, i.e., 3 µM of Aβ and 1.5 µM of IgG; up triangle refers to substoich IgG, i.e., 3 µM of A3 and 0.5 µM of IgG). IgG itself (down triangle) has no effect. FIG. 2B shows Example Compound 2, which inhibits oligomer effects on membrane trafficking. FIG. 2C shows representative micrographs of 21 DIV hippocampal neurons in vitro showing oligomer effects membrane trafficking (corresponding to data point 3 µM in FIG. 2A); and FIG. 2D shows blockade by anti-Abeta antibodies (corresponding to the circle in FIG. 2A). Data were the average of 3 experiments. Scale bar=20 micron in FIG. 2D.

Example EE

Fear Conditioning Assay

Figure 3:
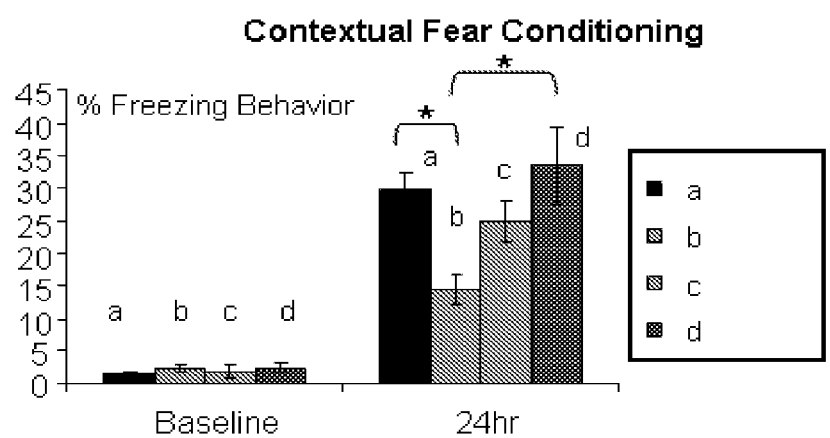
FIG. 3 shows Compound Example 2 inhibiting the memory loss effects of a processed product of amyloid precursor protein.

Compound Example 2 was tested in an animal model of a memory-dependent behavioral task known as fear conditioning. The study protocol was designed based on published protocols (See e.g. Puzzo D, Privitera L, Leznik E, Fà M, Staniszewski A, Palmeri A, Arancio O. Picomolar amyloid-beta positively modulates synaptic plasticity and memory in hippocampus. J Neurosci. 2008 Dec. 31; 28(53)14537-45.). The formation of contextual memories is dependent upon the integrity of medial temporal lobe structures such as the hippocampus. In this assay mice were trained to remember that a particular salient context (conditioned stimulus; CS) is associated with an aversive event, in this case a mild foot shock (the unconditioned stimulus, US). Animals that show good learning will express an increase in freezing behavior when placed back into the same context. This freezing is absent in a novel context. Increased freezing in the context indicates strong hippocampal-dependent memory formation in animals. Memory tested in Fear Conditioning is sensitive to elevations of soluble Aβ. FIG. 3 shows the results of administration of Abeta oligomers (bar labeled with "a") during training results in memory deficits when animals are tested 24 later, compared to vehicle administration (bar labeled with "b"). Example Compound 2 was effective at stopping Abeta oligomer mediated effects on membrane trafficking (Figure. 3). When administered to animals prior to Abeta oligomer administration, Example Compound 2 blocked oligomer effects on memory in a dose-dependent manner. The compound completely blocked oligomer-mediated memory deficits at the 2 pmol dose (FIG. 3, bar labeled with "d"). This behavioral efficacy demonstrates that the membrane trafficking assay is able to predict which compounds will be efficacious in treating the behavioral memory loss caused by oligomers. The fear condition model for memory was performed as described herein.

FIG. 3 shows that Abeta produces significant deficits in memory formation vs. vehicle ($p<0.05$) in the contextual fear conditioning memory task. FIG. 3 shows that the 2 pmol dose of Compound Example 2+Abeta (200 nM) completely blocked the effect of Abeta on memory ($p<0.05$, one way ANOVA, post hoc comparison with Bonferroni correction). No effect of compound alone was observed (data not shown). No adverse behavioral changes were observed at any dose.

Example FF

Membrane Trafficking Assay

Figure 4:
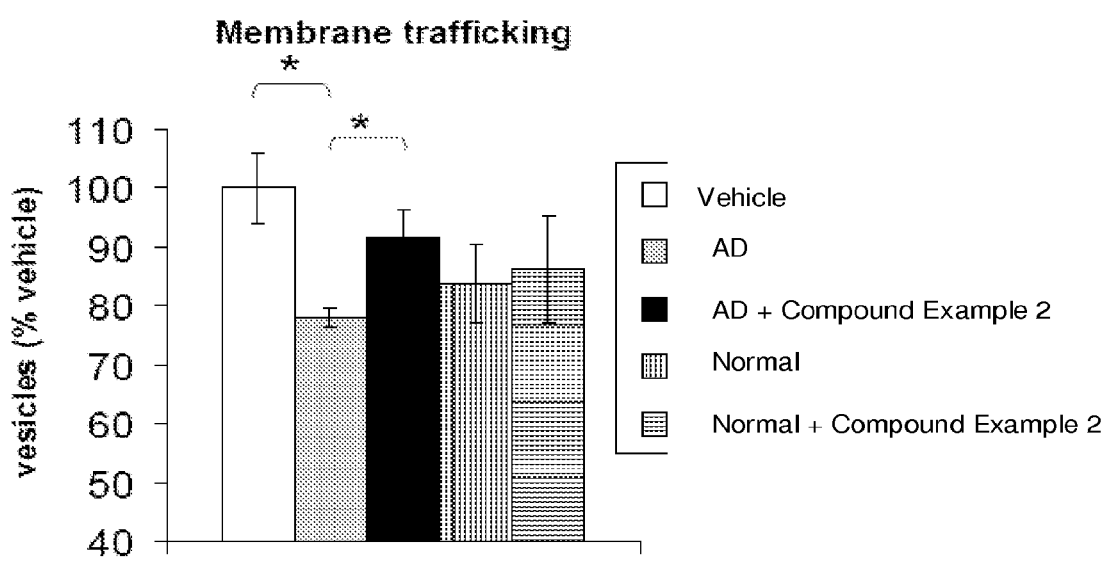
FIG. 4 shows Compound Example 2 inhibiting the membrane trafficking effects of Abeta assemblies isolated from AD patients.

Abeta assemblies were isolated from patients with Alzheimer's Disease (AD) or from normal patients. The Abeta assemblies were tested for their ability to modulate membrane trafficking. HMW (>100 KDa) Abeta assemblies isolated from AD patients do not affect membrane trafficking (not shown). IMW (10-100 KDa) Abeta assemblies isolated from AD patients significantly affect membrane trafficking. (FIG. 4). IMW Abeta assemblies isolated from Age-matched normal individuals do not affect membrane trafficking (FIG. 4). Compound Example 2 has no effect on Abeta assemblies isolated from Age-matched normal individuals. (FIG. 4). Compound Example 2 significantly blocked the trafficking effects of AD-brain derived Abeta assemblies. (FIG. 4).

Although the present invention has been described in considerable detail with reference to certain preferred versions thereof, other versions are possible. Therefore, the spirit and scope of the invention should not be limited to the description of the preferred versions described herein.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the invention, in addition to those described herein, will be apparent to those skilled in the art from the foregoing description. Such modifications are also intended to fall within the scope of the appended claims.

Each reference cited in the present application is herein incorporated by reference in its entirety.

What is claimed is:

1. A method of treating, Alzheimer's disease in a patient comprising administering to the patient a therapeutically effective amount of a compound according to Formula I:

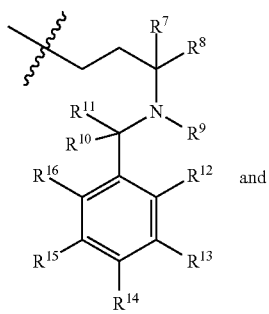

or a pharmaceutically acceptable salt thereof, wherein:
$R^1$ is selected from (A1) and (A2):

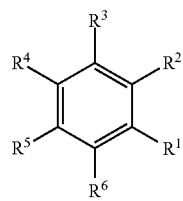

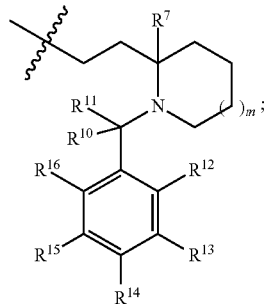

$R^2$, $R^3$, $R^4$, $R^5$, and $R^6$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), $C(O)OR^a$, $C(O)R^b$, $C(O)NR^cR^d$, $OC(O)R^b$, $OC(O)NR^cR^d$, $NR^cR^d$, $NR^cC(O)R^b$, $NR^cC(O)OR^a$, $NR^cS(O)_2R^b$, $NR^cS(O)$, $NR^cR^d$, $S(O)R^b$, $S(O)_2R^b$, and $S(O)_2NR^cR^d$;

$R^7$ is H, $C_{1-6}$ alkyl, $C_{1-6}$ haloalkyl, or $C_{3-7}$ cycloalkyl;
$R^8$ is $C_{1-6}$ alkyl, $C_{1-6}$ haloalkyl, or $C_{3-7}$ cycloalkyl;
$R^9$ is H, $C_{1-6}$ alkyl, $C_{1-6}$ haloalkyl, or $C_{3-7}$ cycloalkyl;
$R^{10}$ is H, $C_{1-6}$ alkyl, $C_{1-6}$ haloalkyl, or $C_{3-7}$ cycloalkyl;
$R^{11}$ is H, $C_{1-6}$ alkyl, $C_{1-6}$ haloalkyl, or $C_{3-7}$ cycloalkyl;
$R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl$)_2$, $NHC(O)(C_{1-4}$ alkyl), SH, $S(C_{1-6}$ alkyl), $C(O)OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{a1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{b1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

$R^{c1}$ and $R^{d2}$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl; and m is 0, 1, or 2, with the proviso that
(a) when $R^1$ is a moiety of (A1), then two of $R^2$, $R^3$, $R^4$, $R^5$, and $R^6$ are independently selected from OH, $C_{1-6}$ alkoxy, and $C_{1-6}$ haloalkoxy; and
(b) when $R^1$ is a moiety of (A1), then at least one of $R^{12}$, $R^{13}$, $R^{14}$, $R^{15}$, and $R^{16}$ is other than H.

2. A method of inhibiting or abating binding of one or more Abeta oligomers to a neuronal cell, comprising contacting the neuronal cell with an effective amount of an amyloid beta oligomer inhibitory compound according to Formula I:

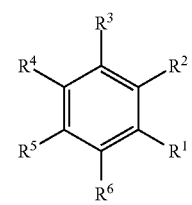

I or a pharmaceutically acceptable salt thereof, wherein:
$R^1$ is selected from (A1) and (A2):

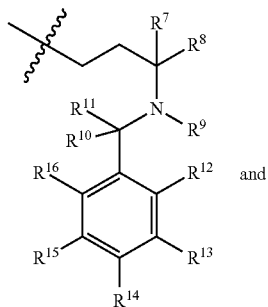

(A1)

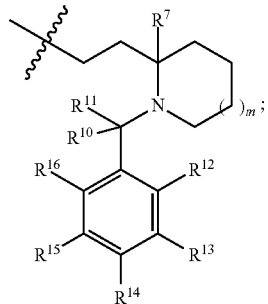

(A2)

$R^2$, $R^3$, $R^4$, $R^5$, and $R^6$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl)$_2$, $NHC(O)(C_{1-4}$ alkyl), SH, $S(C_{1-6}$ alkyl), $C(O)OR^a$, $C(O)R^b$, $C(O)NR^cR^d$, $OC(O)R^b$, $OC(O)NR^cR^d$, NR$^c$R$^d$, NR$^c$C(O)R$^b$, NR$^c$C(O)OR$^a$, NR$^c$S(O)$_2$R$^b$, NR$^c$S(O)$_2$NR$^c$R$^d$, S(O)R$^b$, S(O)$_2$R$^b$, and S(O)$_2$NR$^c$R$^d$;

R$^7$ is H, C$_{1-6}$ alkyl, C$_{1-6}$ haloalkyl, or C$_{3-7}$ cycloalkyl;
R$^8$ is C$_{1-6}$ alkyl, C$_{1-6}$ haloalkyl, or C$_{3-7}$ cycloalkyl;
R$^9$ is H, C$_{1-6}$ alkyl, C$_{1-6}$ haloalkyl, or C$_{3-7}$ cycloalkyl;
R$^{10}$ is H, C$_{1-6}$ alkyl, C$_{1-6}$ haloalkyl, or C$_{3-7}$ cycloalkyl;
R$^{11}$ is H, C$_{1-6}$ alkyl, C$_{1-6}$ haloalkyl, or C$_{3-7}$ cycloalkyl;
R$^{12}$, R$^{13}$, R$^{14}$, R$^{15}$, and R$^{16}$ are each, independently, selected from H, OH, C$_{1-6}$ alkoxy, C$_{1-6}$ haloalkoxy, halo, CN, NO$_2$, C$_{1-6}$ alkyl, C$_{1-6}$ haloalkyl, C$_{3-7}$ cycloalkyl, NH$_2$, NH(C$_{1-4}$ alkyl), NH(C$_{3-7}$ cycloalkyl), N(C$_{1-4}$ alkyl)$_2$, NHC(O)(C$_{1-4}$ alkyl), SH, S(C$_{1-6}$ alkyl), C(O)OR$^{a1}$, C(O)R$^{b1}$, C(O)NR$^{c1}$R$^{d1}$, OC(O)R$^{b1}$, OC(O)NR$^{c1}$, R$^{d1}$, NR$^{c1}$R$^{d1}$, NR$^{c1}$C(O)R$^{b1}$, NR$^{c1}$C(O)OR$^{a1}$, NR$^{c1}$S(O)$_2$R$^{b1}$, NR$^{c1}$S(O)$_2$NR$^{c1}$R$^{d1}$, S(O)R$^{b1}$, S(O)$_2$R$^{b1}$, and S(O)$_2$NR$^{c1}$R$^{d1}$;

each R$^a$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl is optionally substituted with 1, 2, 3, 4, or 5 substituents independently selected from OH, CN, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl and heterocycloalkyl;

each R$^b$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl and heterocycloalkyl;

R$^c$ and R$^d$ are independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl and heterocycloalkyl;

or R$^c$ and R$^d$ together with the N atom to which they are attached form a 4-, 5-, 6- or 7-membered heterocycloalkyl group that is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl;

each R$^{a1}$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl is optionally substituted with 1, 2, 3, 4, or 5 substituents independently selected from OH, CN, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl;

each R$^{b1}$ is independently selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl;

R$^{c1}$ and R$^{d2}$ are independently selected from H, C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the C$_{1-10}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$haloalkoxy, aryl, arylalkyl, heteroaryl, heteroarylalkyl, cycloalkyl, and heterocycloalkyl;

or R$^{c1}$ and R$^{d1}$ together with the N atom to which they are attached form a 4-, 5-, 6- or 7-membered heterocycloalkyl group that is optionally substituted with 1, 2, 3, 4, or 5 substituents independently selected from OH, amino, halo, C$_{1-6}$ alkyl, C$_{1-6}$ haloalkyl, C$_{1-6}$ alkoxy, C$_{1-6}$ haloalkoxy, aryl, arylalkyl, heteroaryl, heteroarylalkyl, cycloalkyl, and heterocycloalkyl; and m is 0, 1, or 2, with the proviso that
(a) when R$^1$ is a moiety of (A1), then two of R$^2$, R$^3$, R$^4$, R$^5$, and R$^6$ are independently selected from OH, C$_{1-6}$alkoxy, and C$_{1-6}$haloalkoxy; and
(b) when R$^1$ is a moiety of (A1), then at least one of R$^{12}$, R$^{13}$, R$^{14}$, R$^{15}$, and R$^{16}$ is other than H.

3. The method of claim 1 or 2, wherein the compound according to formula I, or pharmaceutically acceptable salt thereof, comprises a compound,
or pharmaceutically acceptable salt thereof, wherein
R$^2$, R$^3$, R$^4$, R$^5$, and R$^6$ are each, independently, selected from H, OH, C$_{1-6}$ alkoxy, C$_{1-6}$ haloalkoxy, halo, CN, NO$_2$, C$_{1-6}$alkyl, C$_{1-6}$haloalkyl, C$_{3-7}$ cycloalkyl, NH$_2$, NH(C$_{1-4}$ alkyl), NH(C$_{3-7}$ cycloalkyl), N(C$_{1-4}$alkyl)$_2$, NHC(O)(C$_{1-4}$ alkyl), SH, S(C$_{1-6}$alkyl), C(O)OH, C(O)O(C$_{1-4}$ alkyl), C(O)(C$_{1-4}$ alkyl), and C(O)NH(C$_{1-4}$ alkyl).

4. The method of claim 1 or 2, wherein the amyloid beta oligomer inhibitory compound according to formula I, or pharmaceutically acceptable salt thereof, comprises a compound, or pharmaceutically acceptable salt thereof, wherein
one of $R^2$, $R^3$, $R^4$, $R^5$, and $R^6$ is OH; and
one of $R^2$, $R^3$, $R^4$, $R^5$, and $R^6$ is $C_{1-3}$ alkoxy or $C_{1-3}$ haloalkoxy.

5. The method of claim 1 or 2, wherein the amyloid beta oligomer inhibitory compound according to formula I, or pharmaceutically acceptable salt thereof, comprises a compound, or pharmaceutically acceptable salt thereof, wherein
one of $R^2$, $R^3$, $R^4$, $R^5$, and $R^6$ is OH; and
one of $R^2$, $R^3$, $R^4$, $R^5$, and $R^6$ is methoxy or trihalomethoxy.

6. The method of claim 1 or 2, wherein the amyloid beta oligomer inhibitory compound according to formula I, or pharmaceutically acceptable salt thereof, comprises a compound, or pharmaceutically acceptable salt thereof, wherein
$R^4$ is OH;
$R^5$ is methoxy; and
$R^2$, $R^3$, and $R^6$ are each H.

7. The method of claim 1 or 2, wherein the amyloid beta oligomer inhibitory compound according to formula I, or pharmaceutically acceptable salt thereof, comprises a compound, or pharmaceutically acceptable salt thereof, wherein
$R^7$ is H or $C_{1-6}$ alkyl;
$R^8$ is $C_{1-6}$ alkyl; and
$R^9$ is H or $C_{1-6}$ alkyl.

8. The method of claim 1 or 2, wherein the amyloid beta oligomer inhibitory compound according to formula I, or pharmaceutically acceptable salt thereof, comprises a compound, or pharmaceutically acceptable salt thereof, wherein
$R^{10}$ is H or $C_{1-6}$ alkyl; and
$R^{11}$ is H or $C_{1-6}$ alkyl.

9. The method of claim 1 or 2, wherein the amyloid beta oligomer inhibitory compound according to formula I, or pharmaceutically acceptable salt thereof, comprises a compound, or pharmaceutically acceptable salt thereof, wherein
$R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl)$_2$, $NHC(O)(C_{1-4}$ alkyl), SH, $S(C_{1-6}$ alkyl), C(O)OH, $C(O)O(C_{1-4}$ alkyl), $C(O)(C_{1-4}$ alkyl), and $C(O)NH(C_{1-4}$ alkyl).

10. The method of claim 1 or 2, wherein the amyloid beta oligomer inhibitory compound according to formula I, or pharmaceutically acceptable salt thereof, comprises a compound, or pharmaceutically acceptable salt thereof, wherein
at least one of $R^{12}$, $R^{13}$, $R^{14}$, $R^{15}$, and $R^{16}$ is selected from halo, CN, $NO_2$, $C_{1-6}$ haloalkyl, $C(O)O(C_{1-4}$ alkyl), $C(O)(C_{1-4}$ alkyl), and $C(O)NH(C_{1-4}$ alkyl).

11. The method of claim 1 or 2, wherein the amyloid beta oligomer inhibitory compound according to formula I, or pharmaceutically acceptable salt thereof, comprises a compound, or pharmaceutically acceptable salt thereof, wherein
at least one of $R^{12}$, $R^{13}$, $R^{14}$, $R^{15}$, and $R^{16}$ is selected from halo and $C_{1-6}$ haloalkyl.

12. The method of claim 1 or 2, wherein the amyloid beta oligomer inhibitory compound according to formula I, or pharmaceutically acceptable salt thereof, comprises a compound, or pharmaceutically acceptable salt thereof, wherein
$R^{14}$ is halo or $C_{1-6}$ haloalkyl.

13. The method according to claim 2, wherein the amyloid beta oligomer inhibitory compound according to formula I is selected from 4-(3-(4-chlorobenzylamino)butyl)-2-methoxyphenol or 4-(3-(4-(trifluoromethyl)benzylamino)butyl)-2-methoxyphenol, or a pharmaceutically acceptable salt thereof.

14. The method according to claim 2, wherein the neuronal cell is contacted with the amyloid beta oligomer inhibitory compound, or pharmaceutically acceptable salt thereof, in an amount effective to inhibit or abate activity of Abeta oligomers on the neuronal cell; and/or inhibit or abate membrane trafficking deficits in the neuronal cell, said membrane trafficking effects being associated with exposure of said cell to soluble Abeta oligomers.

15. The method according to claim 14, wherein the cell is contacted by the amyloid beta oligomer inhibitory compound, or pharmaceutically acceptable salt thereof, in an amount effective to inhibit or abate membrane trafficking deficits in said cell, said membrane trafficking effects being associated with exposure of said cell to soluble Abeta oligomers; wherein the compound does not significantly alter membrane trafficking when dosed in the absence of the Abeta oligomers.

16. A method to inhibit, treat, or abate the activity/effect of an Abeta oligomer on a neuronal cell, the method comprising administering an effective amount of a composition comprising
a. a compound of formula I:

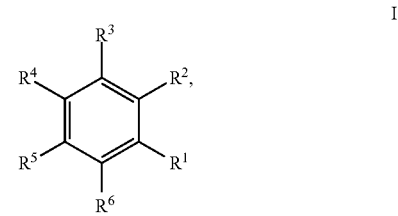

I or a pharmaceutically acceptable salt thereof; and
b. a pharmaceutically acceptable carrier, wherein $R^1$ is selected from (A1) and (A2):

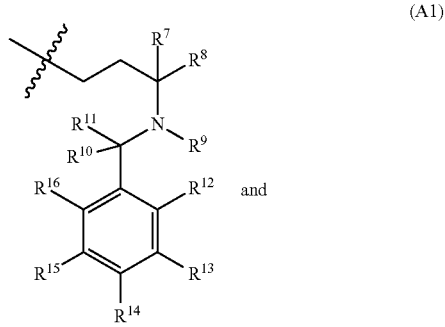

(A1)

and

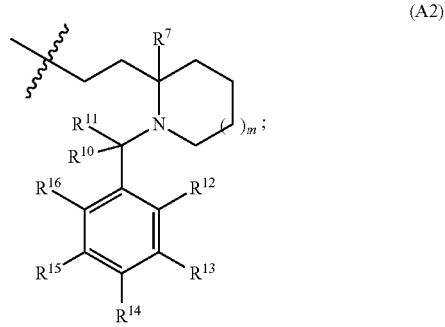

(A2)

$R^2$, $R^3$, $R^4$, $R^5$, and $R^6$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl)$_2$, $NHC(O)(C_{1-4}$ alkyl), SH, $S(C_{1-6}$ alkyl), $C(O)OR^a$, C(O)

$R^b$, $C(O)NR^cR^d$, $OC(O)R^b$, $OC(O)NR^cR^d$, $NR^cR^d$, $NR^cC(O)R^b$, $NR^cC(O)OR^a$, $NR^cS(O)_2R^b$, $NR^cS(O)_2NR^cR^d$, $S(O)R^b$, $S(O)_2R^b$, and $S(O)_2NR^cR^d$;

$R^7$ is H, $C_{1-6}$ alkyl, $C_{1-6}$ haloalkyl, or $C_{3-7}$ cycloalkyl;

$R^8$ is $C_{1-6}$ alkyl, $C_{1-6}$ haloalkyl, or $C_{3-7}$ cycloalkyl;

$R^9$ is H, $C_{1-6}$ alkyl, $C_{1-6}$ haloalkyl, or $C_{3-7}$ cycloalkyl;

$R^{10}$ is H, $C_{1-6}$ alkyl, $C_{1-6}$ haloalkyl, or $C_{3-7}$ cycloalkyl;

$R^{11}$ is H, $C_{1-6}$ alkyl, $C_{1-6}$ haloalkyl, or $C_{3-7}$ cycloalkyl;

$R^{12}$, $R^{13}$, $R^{14}$, $R^{15}$, and $R^{16}$ are each, independently, selected from H, OH, $C_{1-6}$ alkoxy, $C_{1-6}$ haloalkoxy, halo, CN, $NO_2$, $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), $N(C_{1-4}$ alkyl)$_2$, $NHC(O)(C_{1-4}$ alkyl), SH, $S(C_{1-6}$ alkyl), $C(O)OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{a1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents independently selected from OH, CN, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

each $R^{b1}$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

$R^{c1}$ and $R^{d2}$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is optionally substituted with 1, 2, 3, 4, or 5 substituents independently selected from OH, amino, halo, $C_{1-6}$ alkyl, $C_{1-6}$ haloalkyl, $C_{1-6}$ alkoxy, $C_{1-6}$ haloalkoxy, aryl, arylalkyl, heteroaryl, heteroarylalkyl, cycloalkyl, and heterocycloalkyl; and m is 0, 1, or 2, with the proviso that
 (a) when $R^1$ is a moiety of (A1), then two of $R^2$, $R^3$, $R^4$, $R^5$, and $R^6$ are independently selected from OH, $C_{1-6}$ alkoxy, and $C_{1-6}$ haloalkoxy; and
 (b) when $R^1$ is a moiety of (A1), then at least one of $R^{12}$, $R^{13}$, $R^{14}$, $R^{15}$, and $R^{16}$ is other than H.

17. The method according to claim 16, wherein the compound is administered in an amount effective to:
 (i) restore long term potentiation;
 (ii) inhibit or abate neurodegeneration;
 (iii) inhibit or abate-Abeta oligomer binding to said neuronal cell; and/or
 (iv) inhibit or abate Abeta-mediated effects in membrane trafficking in said neuronal cell, said membrane trafficking effects being associated with exposure of said cell to soluble Abeta oligomers.

18. The method according to claim 17, wherein the compound is administered in an amount effective to inhibit or abate Abeta-mediated effects in membrane trafficking in said neuronal cell, said membrane trafficking effects being associated with exposure of said cell to soluble Abeta oligomers, but wherein the compound does not significantly affect membrane trafficking when dosed alone.

19. The method according to claim 17, wherein the compound is administered in an amount effective to inhibit or abate Abeta oligomer binding to said neuronal cell.

20. A method of treating Alzheimer's disease in a patient comprising administering to the patient a therapeutically effective amount of a compound selected from 4-(3-(4-chlorobenzylamino)butyl)-2-methoxyphenol or 4-(3-(4-(trifluoromethyl)benzylamino)butyl)-2-methoxyphenol, or a pharmaceutically acceptable salt thereof.

* * * * *